US012066439B2

(12) United States Patent
Fiechtner et al.

(10) Patent No.: US 12,066,439 B2
(45) Date of Patent: *Aug. 20, 2024

(54) METHODS FOR ENHANCING SPECIFICITY AND SENSITIVITY OF GROUP A *STREPTOCOCCUS* IMMUNOASSAY

(71) Applicant: Becton, Dickinson and Company, Franklin Lakes, NJ (US)

(72) Inventors: Michael D. Fiechtner, Poway, CA (US); Huimiao Ren, San Diego, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/823,473

(22) Filed: Aug. 30, 2022

(65) Prior Publication Data

US 2023/0003729 A1 Jan. 5, 2023

Related U.S. Application Data

(63) Continuation of application No. PCT/US2022/022843, filed on Mar. 31, 2022.

(60) Provisional application No. 63/169,555, filed on Apr. 1, 2021.

(51) Int. Cl.
*G01N 33/569* (2006.01)
*G01N 33/53* (2006.01)
*G01N 33/543* (2006.01)

(52) U.S. Cl.
CPC ... *G01N 33/56944* (2013.01); *G01N 33/5306* (2013.01); *G01N 33/54386* (2013.01); *G01N 33/54388* (2021.08); *G01N 33/54393* (2013.01)

(58) Field of Classification Search
CPC ......... G01N 33/5306; G01N 33/54386; G01N 33/56944; G01N 33/54393; G01N 33/54388; G01N 2469/10; G01N 2470/04; G01N 2800/52
See application file for complete search history.

(56) References Cited

U.S. PATENT DOCUMENTS

| | | | |
|---|---|---|---|
| 4,857,453 A | 8/1989 | Ullman et al. |
| 5,415,994 A | 5/1995 | Imrich et al. |
| 5,604,109 A | 2/1997 | Fischetti et al. |
| 5,763,262 A | 6/1998 | Wong et al. |
| 5,770,460 A | 6/1998 | Pawlak et al. |
| 7,465,587 B2 | 12/2008 | Imrich et al. |
| 7,601,546 B2 | 10/2009 | Bayloff et al. |
| 9,207,181 B2 | 12/2015 | Egan et al. |
| 10,168,329 B2 | 1/2019 | Ren et al. |
| 2004/0137554 A1 | 7/2004 | Lambert et al. |
| 2005/0181388 A1 | 8/2005 | Edwards et al. |
| 2005/0250196 A1 | 11/2005 | Paton et al. |
| 2008/0014657 A1 | 1/2008 | Lovell et al. |
| 2009/0305231 A1 | 12/2009 | Weidemaier et al. |
| 2010/0022509 A1 | 1/2010 | Fahey et al. |
| 2010/0247571 A1 | 9/2010 | Wong et al. |
| 2013/0196337 A1 | 8/2013 | Ren et al. |
| 2020/0116720 A1 | 4/2020 | Ren et al. |
| 2022/0317124 A1* | 10/2022 | Fiechtner ............ G01N 33/5306 |

FOREIGN PATENT DOCUMENTS

| | | | | |
|---|---|---|---|---|
| AU | 198538104 A | 8/1985 | | |
| AU | 711947 B2 | 10/1999 | | |
| CN | 1083112 A | 3/1994 | | |
| CN | 1543338 A | 11/2004 | | |
| EP | 869801 B1 | 1/2004 | | |
| EP | 1879028 B1 | 1/2008 | | |
| EP | 2031392 A1 | 3/2009 | | |
| EP | 2739975 A1 * | 6/2014 | ....... | G01N 33/54393 |
| FR | 2684110 A1 | 5/1993 | | |
| GB | 2195343 A | 4/1988 | | |
| JP | H02-177899 A | 7/1990 | | |
| JP | H03-152466 A | 6/1991 | | |
| JP | H06-18524 A | 1/1994 | | |
| JP | H07-36018 B2 | 4/1995 | | |
| JP | H08-240592 A | 9/1996 | | |
| JP | 2601498 B2 | 4/1997 | | |
| JP | 2001289851 A | 10/2001 | | |
| JP | 2009541281 A | 11/2009 | | |
| SG | 121654 A1 | 5/2006 | | |
| WO | WO 1984/004169 A | 10/1984 | | |

(Continued)

OTHER PUBLICATIONS

Gu et al., "Synthesis and Immunological Characterization of Modified Hyaluronic Acid Hexasaccharide Conjugates", J Org Chem. (2013) 78: 8004-8019.

Altman et al., "Diagnostic Tests 2: Predictive Values", BMJ (1994) 309(6947): 102.

Blank et al., "Overlapping humoral autoimmunity links rheumatic fever and the antiphospholipid syndrome". Rheumatol. Jul. 2006; 45(7): 833-841.

Boeggeman, "Site specific conjugation of fluoroprobes to the remodeled Fc N-glycans of monoclonal antibodies using mutant glycosyltransferases: application for cell surface antigen detection". Bioconjug Chem. Jun. 2009; 20(6): 1226-1236.

(Continued)

*Primary Examiner* — Shafiqul Haq
(74) *Attorney, Agent, or Firm* — Knobbe, Martens, Olson & Bear, LLP

(57) ABSTRACT

The present disclosure provides methods and kits for detecting Group A *Streptococcus* in biological samples. More particularly, the present disclosure provides methods for enhancing the specificity and sensitivity of Group A *Streptococcus* immunoassays by including N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine. The methods and kits disclosed herein are thus useful for reliable and early diagnosis of streptococcal infections in a subject.

22 Claims, 13 Drawing Sheets

(56) References Cited

FOREIGN PATENT DOCUMENTS

| WO | WO 1988/002781 A1 | 4/1988 |
|---|---|---|
| WO | WO 1988/004431 A1 | 6/1988 |
| WO | WO 1990/010232 A1 | 9/1990 |
| WO | WO 1995/004280 A1 | 2/1995 |
| WO | WO 1999/005524 A1 | 2/1999 |
| WO | WO 2006/093524 A2 | 9/2006 |
| WO | WO 2008/073895 A2 | 6/2008 |
| WO | WO 2012/131386 A1 | 10/2012 |
| WO | WO 2013/116831 A1 | 8/2013 |
| WO | WO 2014/025415 A2 | 2/2014 |
| WO | WO 2014/057159 A1 | 4/2014 |
| WO | WO 2014/178062 A2 | 11/2014 |
| WO | WO 2017/138946 A1 | 8/2017 |
| WO | WO 2017/140686 A1 | 8/2017 |
| WO | WO 2019/153934 A1 | 8/2019 |
| WO | WO 2019/162496 A1 | 8/2019 |
| WO | WO 2019/215199 A1 | 11/2019 |
| WO | WO 2019/238500 A1 | 12/2019 |
| WO | WO 2019/246361 A1 | 12/2019 |
| WO | WO 2020/016616 A1 | 1/2020 |
| WO | WO 2020/089188 A1 | 5/2020 |
| WO | WO 2020/161238 A1 | 8/2020 |
| WO | WO 2020/165456 A1 | 8/2020 |
| WO | WO 2021/55127 A1 | 8/2021 |
| WO | WO 2021/155082 A1 | 8/2021 |
| WO | WO 2021/155103 A1 | 8/2021 |
| WO | WO 2021/155105 A1 | 8/2021 |
| WO | WO 2021/155153 A1 | 8/2021 |
| WO | WO 2021/155170 A1 | 8/2021 |

OTHER PUBLICATIONS

Briko et al., "Enzyme immunoassay kit for detecting antibodies to group-specific antigen of group A *Streptococcus* on the base of conjugated N-acetylglucosamine and its medical application". Klinicheskaya Laboratornaya Diagnostika (1997) 9: 43-46; English Abstract only.

Engvall E., "Enzyme Immunoassay ELISA and EMIT", Meth Enzym. (1980) Chapter 28, 70A: 419-439.

Galvin, J. E., "Cytotoxic mAb from rheumatic carditis recognizes heart valves and laminin". J Clin Invest., Jan. 15, 2000; 106(2): 217-224.

Hazenbos et al., "Novel *Staphylococcal* glycosyltransferases SdgA and SdgB mediate immunogenicity and protection of virulence-associated cell wall proteins". PLoS Pathogens; Oct. 10, 2013; 9(10): e1003653 in 18 pages.

Hirota et al., "Cross-reactivity between human sialyl Lewis(x) oligosaccharide and common causative oral bacteria of infective endocarditis". Oct. 1995; 12(2): 159-164.

Kabat et al.[Eds.], Sequences of Proteins of Immunological Interest, 5th Edition, NIH Publication No. 91-3242; (1991), Table of Contents in 28 pages.

Millipore, "Rapid lateral flow test strips". 2008 Lit. No. TB500EN00 Rev. B (May 2008) in 42 pages.

Ohkuni et al., "Culturette brand ten-minute group A Strep ID test in regard to its specificity and sensitivity". J Japanese Assoc Inf Dis., (1985) 59(12): 1204-1209. English Abstract.

Poulsen et al., "Purification and anti *Streptococcus* Group A antibodies by affinity chromatography and isoelectric focusing". Carlsberg Res Commun. (1977) 42:397-405.

International Search Report and Written Opinion dated Jul. 11, 2022 for PCT Application No. PCT/US2022/022843, filed Mar. 31, 2022.

\* cited by examiner

N-propionylglucosamine

2-N-butanoyl-D-glucosamide

Bis(2-(D-2-deoxy-glucosaminyl))-PEG3-amide m-PEG4-glucosamine m-PEG6-glucosamine m-PEG10-glucosamine

METHODS FOR ENHANCING SPECIFICITY AND SENSITIVITY OF GROUP A *STREPTOCOCCUS* IMMUNOASSAY

CROSS-REFERENCE TO RELATED APPLICATIONS

This application claims the benefit of and priority to PCT/US2022/022843, filed Mar. 31, 2022, which claims priority to U.S. Provisional Patent Application No. 63/169,555, filed Apr. 1, 2021, the entire contents of which are incorporated herein by reference.

TECHNICAL FIELD

The present disclosure provides methods for detecting analytes in biological samples. Specifically, the present disclosure provides methods for enhancing the specificity and sensitivity of Group A *Streptococcus* immunoassays by including N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine Kits for use in practicing the methods also are provided.

BACKGROUND

The following description of the background of the present disclosure is provided simply to aid the reader in understanding the disclosure and is not admitted to describe or constitute prior art to the present disclosure.

Detection of microbial pathogens in biological samples is critical in clinical decision-making, as treatment may vary considerably depending upon the causative organism. Acute diseases associated with *S. pyogenes* occur mainly in respiratory tract, bloodstream or skin. Streptococcal disease is most often a respiratory infection (pharyngitis or tonsillitis) or a skin infection (pyoderma). Acute *S. pyogenes* infections may present as pharyngitis (strep throat), scarlet fever (rash), impetigo (infection of the superficial layers of the skin) or cellulitis (infection of the deep layers of the skin). Invasive, toxigenic infections can result in necrotizing fasciitis, joint or bone infections, myositis, meningitis, endocarditis and streptococcal toxic shock syndrome. Patients may also develop immune-mediated post-streptococcal sequelae, such as acute rheumatic fever and acute glomerulonephritis, following acute infections caused by *S. pyogenes*, which occur in 1-3% of untreated infections. These conditions and their pathology are not attributable to dissemination of the bacteria per se, but to aberrant immunological reactions to Group A streptococcal antigens. Due to the occasional cases of rapidly progressive disease and the risk of serious sequelae in untreated infections, *S. pyogenes* remains a major health concern.

Thus, the accurate and rapid identification of Streptococcal infections can be critical to provide prompt and appropriate treatment to patients.

SUMMARY

The present disclosure provides devices, methods and improved diagnostic kits for detecting Group A *Streptococcus* (also referred to herein as "Strep A") in biological samples. More particularly, the present disclosure provides improved immunoassays in which Group A streptococcal infection is detected with a reduced rate of false-positive results and increased sensitivity (i.e., reduced false negative results) via addition of N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine to the assay.

In one aspect, the present disclosure provides a method for detecting the presence of at least one Group A *Streptococcus* species in a biological sample comprising: (a) contacting the biological sample with an antibody or an antigen binding fragment that specifically targets a Group A *Streptococcus*-specific antigen and an effective amount of N-propionyl-D-glucosamine, 2-N-butanoyl-D-glucosamine, Bis-(2-(D-2-deoxy-glucosaminyl))-PEG3-amide, m-PEG4-glucosamine, m-PEG6-glucosamine, or m-PEG10-glucosamine; and (b) detecting binding of the antibody or the antigen binding fragment to the Group A *Streptococcus*-specific antigen, if present, in the sample, wherein detection of binding of the antibody or the antigen binding fragment to the Group A *Streptococcus*-specific antigen indicates the presence of at least one Group A *Streptococcus* species in the sample. In some embodiments, the antibody is a polyclonal antibody. In some embodiments, the antibody is a monoclonal antibody. The Group A *Streptococcus*-specific antigen may be selected from the group consisting of capsular polysaccharide ("C-substance"), cell wall peptidoglycan, lipoteichoic acid (LTA), M protein, fimbrial proteins, fibronectin-binding proteins, and cell-bound streptokinase. Examples of Group A *Streptococcus* species include *Streptococcus pyogenes* or *Streptococcus dysgalactiae*.

Additionally or alternatively, in some embodiments, the antibody or antigen binding fragment comprises a reporter label. A reporter label may be, for example, a gold nanoparticle label, a chemiluminescent label, a radioactive label, a bioluminescent label, a fluorescent label, a chromogenic label, a spectroscopic label, a photochemical label, or an electrochemiluminescent label. Examples of fluorescent labels include, but are not limited to, europium, TagBFP, Azurite, EBFP2, mKalama1, Sirius, Sapphire, T-Sapphire, ECFP, Cerulean, SCFP3A, mTurquoise, monomeric Midoriishi-Cyan, TagCFP, mTFP1, EGFP, Emerald, Superfolder GFP, Monomeric Azami Green, TagGFP2, mUKG, mWasabi, EYFP, Citrine, Venus, SYFP2, TagYFP, Monomeric Kusabira-Orange, mKOK, mKO2, mOrange, mOrange2, mRaspberry, mCherry, dsRed, mStrawberry, mTangerine, tdTomato, TagRFP, TagRFP-T, mApple, mRuby, mPlum, HcRed-Tandem, mKate2, mNeptune, NirFP, TagRFP657, IFP1.4, iRFP, mKeima Red, LSS-mKate1, LSS-mKate2, PA-GFP, PAmCherry1, PATagRFP, Kaede (green), Kaede (red), KikGR1 (green), KikGR1 (red), PS-CFP2, PS-CFP2, mEos2 (green), mEos2 (red), PSmOrange, and Dronpa. Examples of chemiluminescent labels include, but are not limited to, β-galactosidase, horseradish peroxidase (HRP), and alkaline phosphatase. Examples of bioluminescent labels include aequorin, firefly luciferase, *Renilla* luciferase, red luciferase, luxAB, or nanoluciferase. Examples of radioactive labels include $^3$H, $^{14}$C, $^{32}$P, $^{35}$S, $^{57}$Co, $^{131}$I and $^{186}$Re.

In some embodiments of the methods disclosed herein, the biological sample is a body fluid, such as urine, saliva, sputum, mucous, a throat swab sample, blood, blood components such as plasma or serum, amniotic fluid, semen, wound secretions, vaginal secretions, tears, spinal fluid, washings, and other bodily fluids. Biological samples include swab specimens from, e.g., the cervix, urethra, nostril, and throat. In some embodiments, the biological sample is collected through the use of a pharyngeal swab. In some embodiments, the biological sample is collected through a swab of the pharynx, tongue, cheek, teeth, gums or nasal passages.

Additionally or alternatively, in some embodiments of the methods of the present technology, binding of the antibody or the antigen binding fragment to the Group A *Streptococcus*-specific antigen is detected via enzyme-linked immunosorbent assay (ELISA) or Enzyme multiplied immunoassay technique (EMIT).

Additionally or alternatively, in some embodiments, the biological sample is obtained from a subject suffering from or suspected of having a bacterial infection. In certain embodiments, the subject is human.

In one aspect, the present disclosure provides a device for detecting the presence of Group A *Streptococcus* in a sample, comprising: a matrix having (i) a sample receiving zone for receiving a sample containing or suspected of containing a Group A *Streptococcus*-specific antigen, (ii) a labeling zone containing a detector antibody or detector antigen binding fragment for specifically labeling the antigen as it passes there through and (iii) a capture zone having means for specifically binding the labeled antigen thereon, wherein the sample receiving zone, the labeling zone and the capture zone are arranged on the matrix in a liquid flow path, and wherein at least one of the sample receiving zone, the capture zone, and the labeling zone comprise N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine. In some embodiments, the detector antibody is a polyclonal antibody. In some embodiments, the detector antibody is a monoclonal antibody.

In some embodiments of the device, the detector antibody or detector antigen binding fragment comprises a gold nanoparticle label, a chemiluminescent label, a radioactive label, a bioluminescent label, a fluorescent label, a chromogenic label, a spectroscopic label, a photochemical label, or an electrochemiluminescent label.

Additionally or alternatively, in some embodiments, the means for specifically binding the labeled antigen to the capture zone is a capture antibody or capture antigen binding fragment. In certain embodiments, the capture antibody is a polyclonal antibody. In some embodiments, the capture antibody is a monoclonal antibody.

In another aspect, the present disclosure provides methods for selecting a patient for antibiotic therapy. In some embodiments, the method comprises detecting the presence of at least one Group A *Streptococcus* species in a biological sample obtained from the patient using any of the devices disclosed herein; and administering antibiotic therapy to the patient. In other embodiments, the method comprises (a) contacting a biological sample obtained from the patient with an antibody or an antigen binding fragment that specifically targets a Group A *Streptococcus*-specific antigen and an effective amount of N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine; and (b) administering antibiotic therapy to the patient when binding between the antibody or antigen binding fragment and the Group A *Streptococcus*-specific antigen is detected in the sample. In some embodiments of the methods disclosed herein, the antibiotic therapy comprises one or more of penicillin, ampicillin, sulbactam, amoxicillin, clavulanic acid, clindamycin, erythromycin, macrolides, and cephalosporins. In some embodiments, the macrolide-antibiotics are selected from the group consisting of azithromycin (Zithromax), clarithromycin (Biaxin), erythromycin (E-Mycin, Eryc, Ery-Tab, PCE, Pediazole, Ilosone), and roxithromycin. Examples of cephalosporins include Cefacetrile (e.g., cephacetrile), Cefadroxil (e.g., cefadroxyl; Duricef), Cefalexin (e.g., cephalexin; Keflex), Cefaloglycin (e.g., cephaloglycin), Cefalonium (e.g., cephalonium), Cefaloridine (e.g., cephaloradine), Cefalotin (e.g., cephalothin; Keflin), Cefapirin (e.g., cephapirin; Cefadryl), Cefatrizine, Cefazaflur, Cefazedone, Cefazolin (e.g., cephazolin; Ancef, Kefzol), Cefradine (e.g., cephradine; Velosef), Cefroxadine, Ceftezole, Cefaclor (e.g., Ceclor, Distaclor, Keflor, Raniclor), Cefonicid (e.g., Monocid), Cefprozil (e.g., cefproxil; Cefzil), Cefuroxime (e.g., Zefu, Zinnat, Zinacef, Ceftin, Biofuroksym, Xorimax), Cefuzonam, Cefmetazole, Cefotetan, Cefoxitin, Loracarbef (e.g., Lorabid), Cefbuperazone, Cefmetazole (e.g., Zefazone), Cefminox, Cefotetan (e.g., Cefotan), Cefoxitin (e.g., Mefoxin), Cefotiam (e.g., Pansporin), Cefcapene, Cefdaloxime, Cefdinir (e.g., Sefdin, Zinir, Omnicef, Kefnir), Cefditoren, Cefetamet, Cefixime (e.g., Fixx, Zifi, Suprax), Cefmenoxime, Cefodizime, Cefotaxime (e.g., Claforan), Cefovecin (e.g., Convenia), Cefpimizole, Cefpodoxime (e.g., Vantin, PECEF, Simplicef), Cefteram, Ceftamere (e.g., Enshort), Ceftibuten (e.g., Cedax), Ceftiofur (e.g., Naxcel, Excenel), Ceftiolene, Ceftizoxime (e.g., Cefizox), Ceftriaxone (e.g., Rocephin), Cefoperazone (e.g., Cefobid), Ceftazidime (e.g., Meezat, Fortum, Fortaz), Latamoxef (e.g., moxalactam), Cefclidine, Cefepime (e.g., Maxipime), Cefluprenam, Cefoselis, Cefozopran, Cefpirome (e.g., Cefrom), Cefquinome, Flomoxef, Ceftobiprole, Ceftaroline, Ceftolozane, Cefaloram, Cefaparole, Cefcanel, Cefedrolor, Cefempidone, Cefetrizole, Cefivitril, Cefmatilen, Cefmepidium, Cefoxazole, Cefrotil, Cefsumide, Ceftioxide, Cefuracetime, and Nitrocefin.

In another aspect, the present disclosure provides a kit comprising polyclonal and/or monoclonal antibodies that target Group A *Streptococcus*-specific antigens, at least one of N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine, and instructions for use.

Also disclosed herein are kits including: a device comprising a matrix having (i) a sample receiving zone for receiving a sample containing or suspected of containing a Group A *Streptococcus*-specific antigen; (ii) a labeling zone containing a detector antibody for specifically labeling the antigen as it passes there through and (iii) a capture zone having means for specifically binding the labeled antigen thereon, wherein the sample receiving zone, the labeling zone and the capture zone are arranged on the matrix in a liquid flow path; and a container comprising an extraction reagent, wherein at least one of the extraction reagent, the sample receiving zone, the capture zone, and the labeling zone comprise N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine. In certain embodiments, N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine is deposited on the sample receiving zone.

DETAILED DESCRIPTION

Figure 1A:
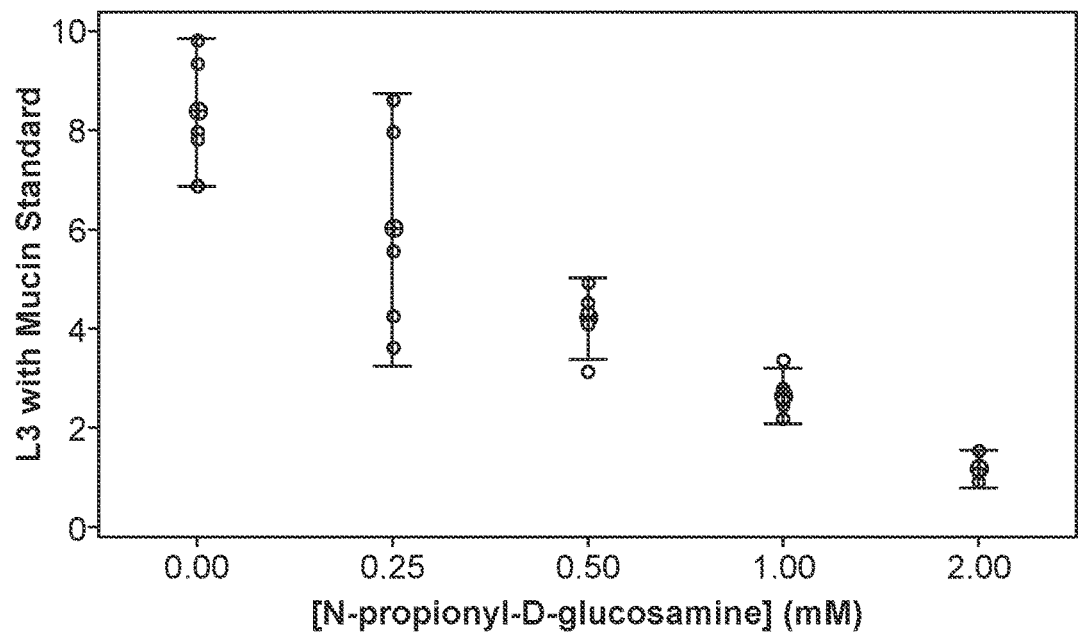
FIGS. 1A-1C show the effect of N-propionyl-D-glucosamine on the sensitivity and false positivity of the Veritor™ Strep A assay when analyzing a test sample. The N-propionyl-D-glucosamine was added to the extraction reagent and mixed with porcine mucin, a surrogate of human mucin from saliva for specificity, or with Strep A extract for sensitivity.
Figure 1B:
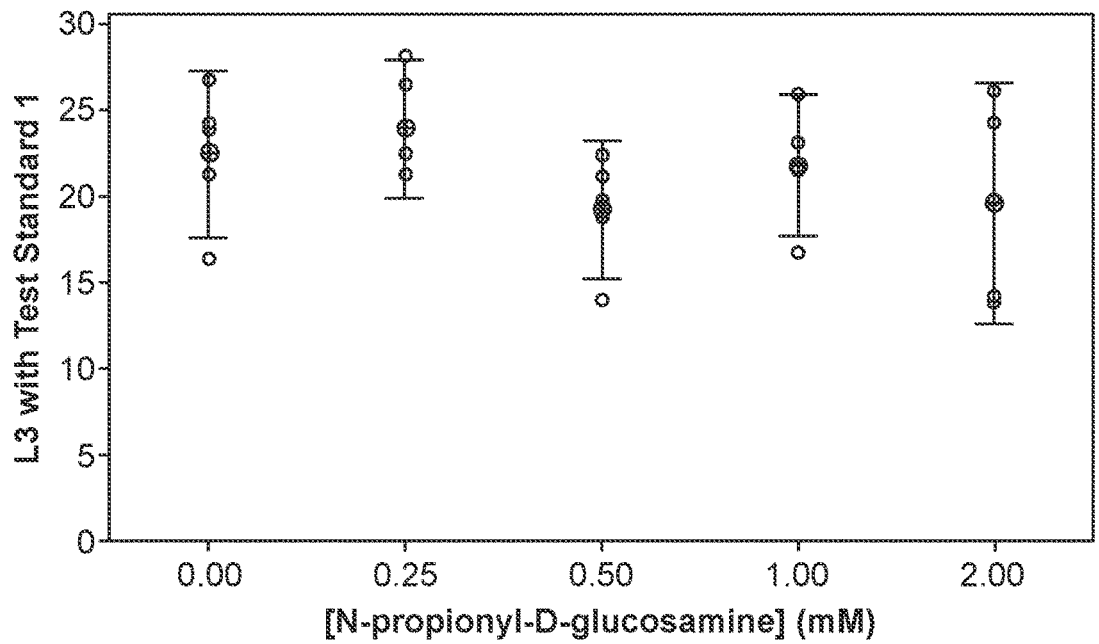
Figure 1C:
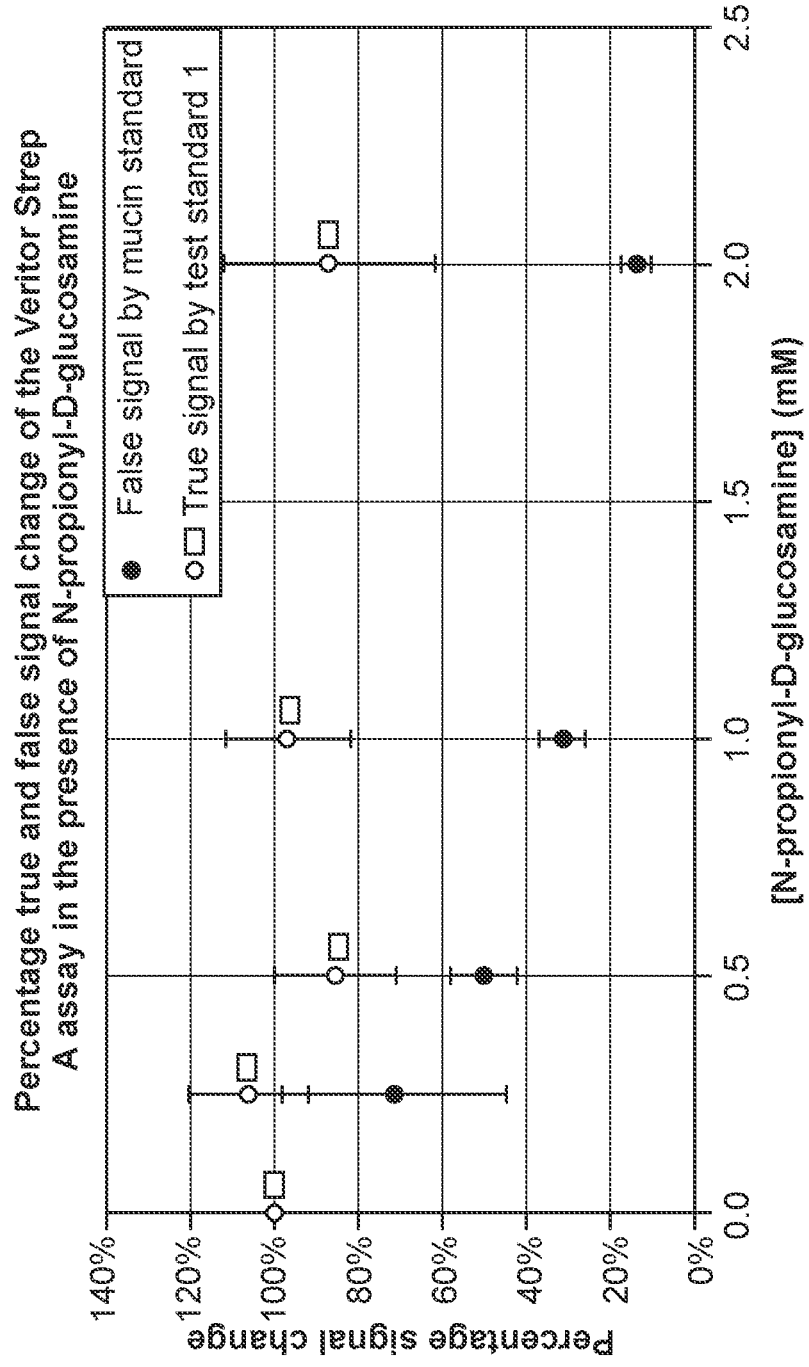
Figure 2:
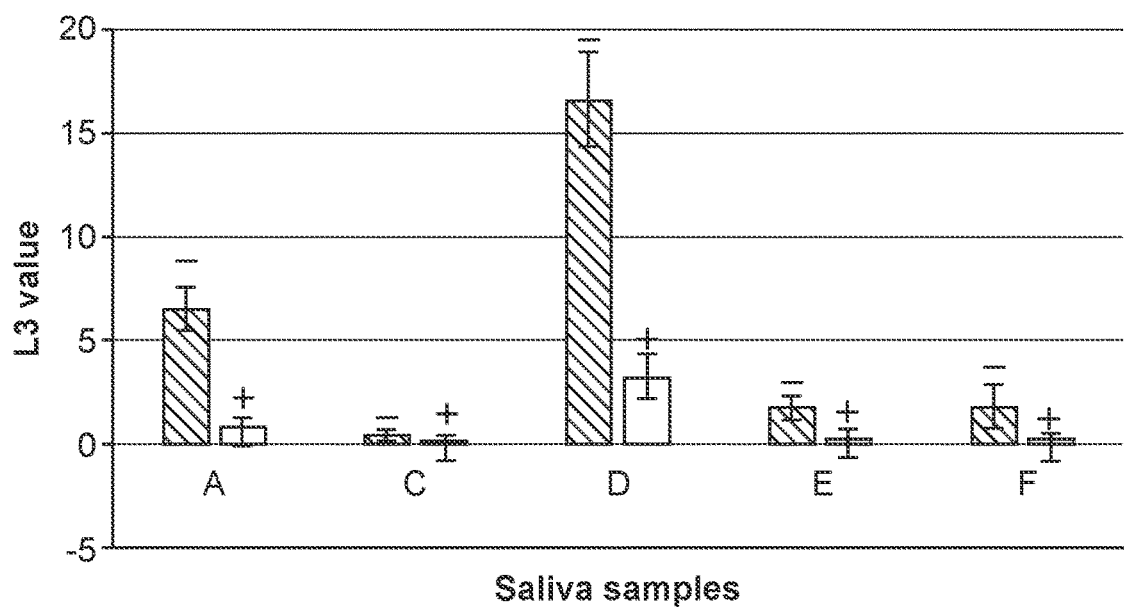
FIG. 2 shows the effect of N-propionyl-D-glucosamine on the false positivity of the Veritor™ Strep A assay caused by a saliva sample.
Figure 3A:
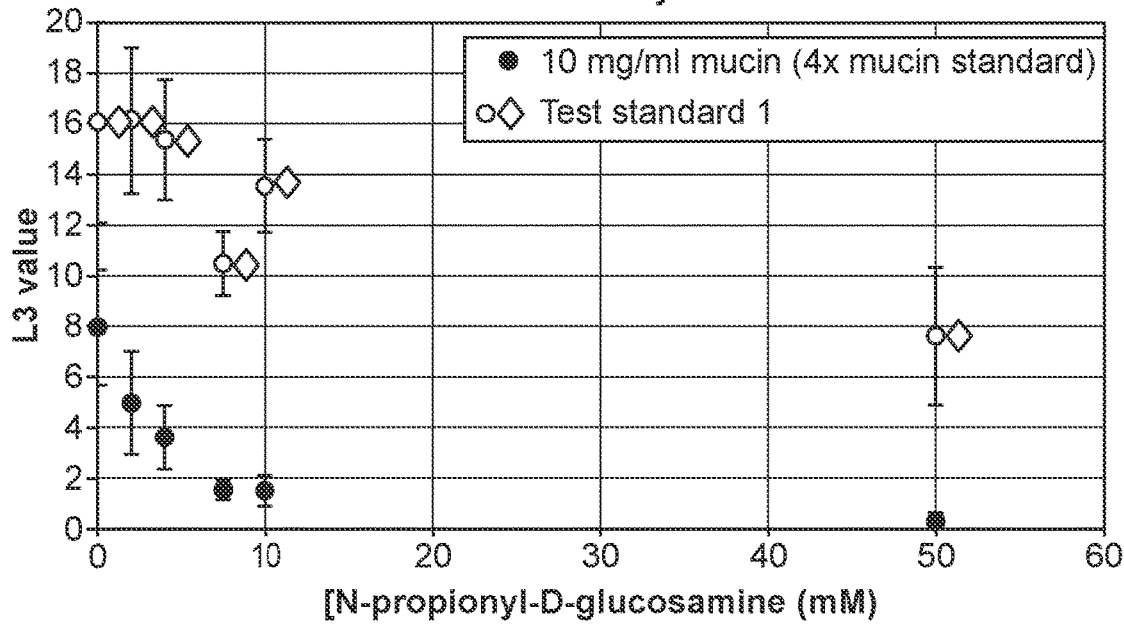
FIGS. 3A-3B show the effect of N-propionyl-D-glucosamine in the conjugate spraying solution (on the conjugate pad) on the sensitivity and specificity of the Veritor™ Strep A assay.
Figure 3B:
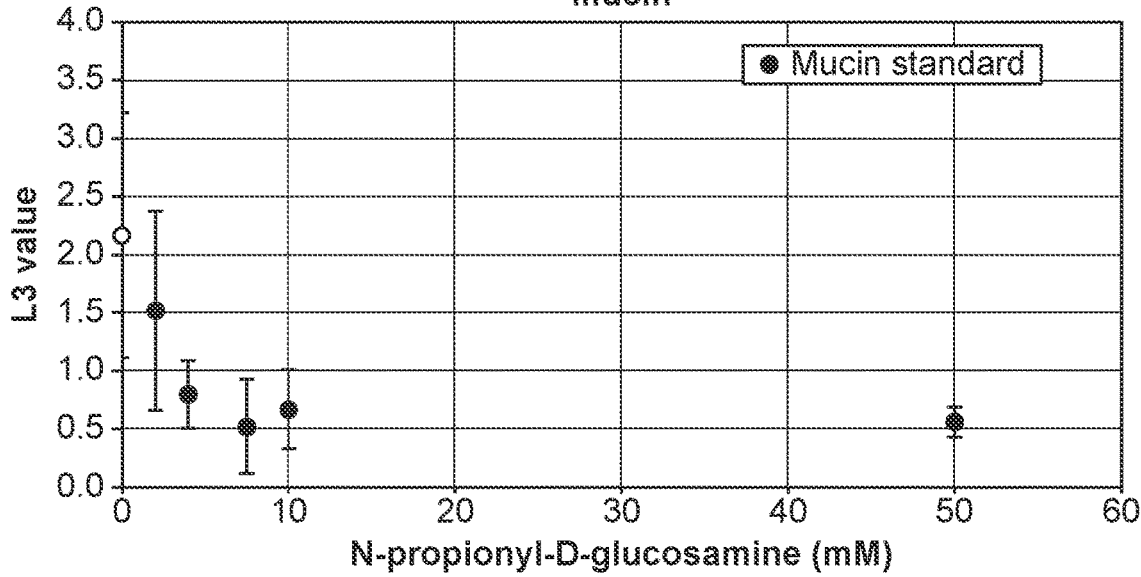
Figure 4:
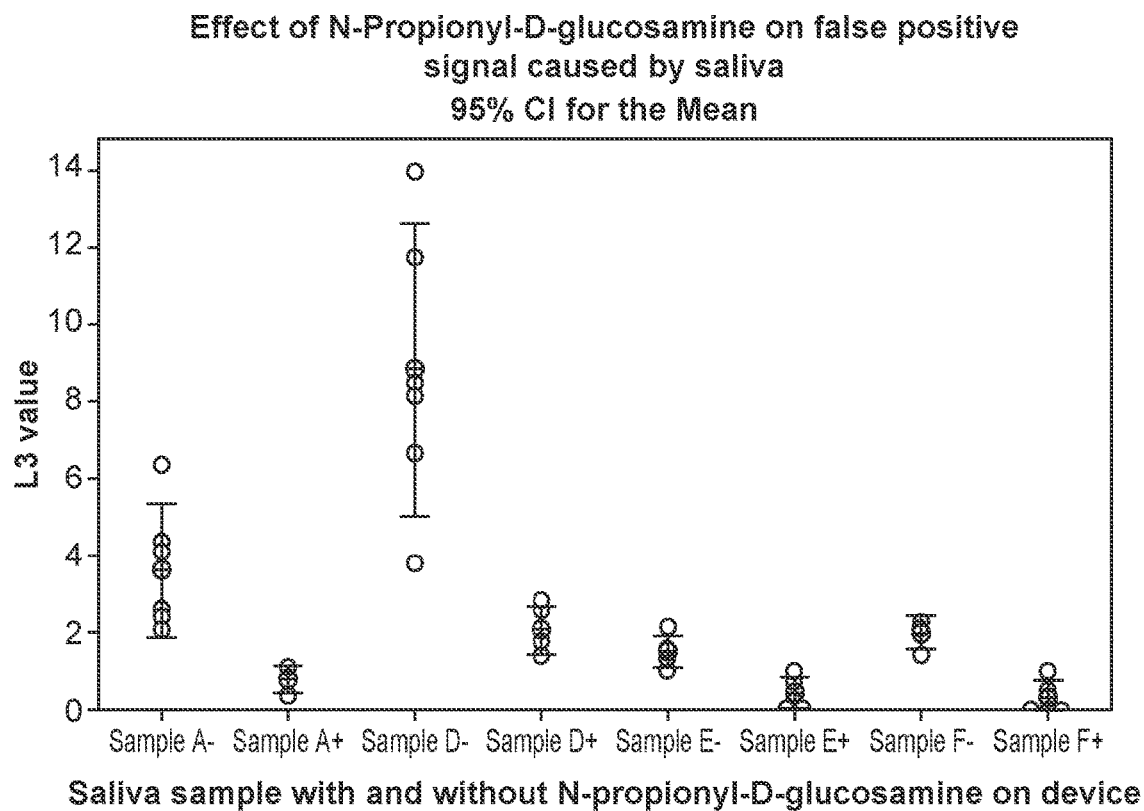
FIG. 4 shows the effect of N-propionyl-D-glucosamine in the conjugate spraying solution (on the conjugate pad) on the false positivity of the Veritor™ Strep A assay caused by saliva.

*Streptococcus pyogenes* (Group A *Streptococcus*) is a Gram-positive, non-motile, non-spore forming bacterium that occurs in chains or in pairs of cells, where individual cells are round-to-ovoid cocci, 0.6-1.0 micrometer in diameter. *S. pyogenes* is one of the most frequent pathogens of humans Approximately 5-15% of normal individuals harbor the bacterium, usually in the respiratory tract, yet remain asymptomatic. As normal flora, *S. pyogenes* can infect when defenses are compromised or when the organisms are able to penetrate the constitutive defenses. The cell surface of *S. pyogenes* accounts for many of the bacterium's determinants of virulence, especially those concerned with colonization and evasion of phagocytosis and the host immune responses. The surface of the bacterium is incredibly complex and chemically-diverse. Antigenic components include capsular polysaccharide (C-substance), cell wall peptidoglycan and lipoteichoic acid (LTA), and a variety of surface proteins, including M protein, fimbrial proteins, fibronectin-binding proteins, (e.g. Protein F) and cell-bound streptokinase.

Rapid methods of diagnosing microbial infections are necessary to provide timely results for guiding clinical therapy. Some of the most effective of these rapid methods have been immunologically based. Monoclonal and polyclonal antibodies to microbe-specific antigens have been developed and used in immunoassays to identify specific microbes in biological samples. For example, immunoassays for the identification of group A streptococcal antigens in human samples are useful for the early detection of *S. pyogenes* infection, so that proper antibiotic therapy may be initiated. Group A *Streptococcus* in pharyngeal exudates can be identified by polyclonal or monoclonal antibodies to antigens specific for Group A *Streptococcus*. One such test is described in U.S. Pat. No. 5,770,460, providing a one-step lateral flow assay for Group A *Streptococcus*-specific antigens. However, tests relying on pharyngeal swabs are often complicated by a high false positive rates. Although instructions for use of pharyngeal swab tests specifically direct the user to avoid contacting the tongue, cheek and/or teeth with the swab, inadvertent contact often occurs, nonetheless.

Epithelial cells originating from the tongue, cheek and/or teeth may contain molecular mimics of one or more components of the *S. pyogenes* cell wall, and a polyclonal antibody specific for Group A *Streptococcus* may bind and "recognize" epitopes on the epithelial cells in a test subject not infected by or carrying Group A strep, resulting in a false positive result. Specifically, salivary mucin and other glycosylated proteins found in the oral cavity contain the sugar, N-acetyl-D-glucosamine, as a glycan constituent. N-acetyl-D-glucosamine is believed to be the immunodominant constituent of the Group A Strep (GAS) carbohydrate antigen epitope. Consequently, the presence of these glycoproteins in a throat swab specimen can cause false positive results in immunoassays designed to detect Group A Strep. Rabbit polyclonal antibodies are commonly used as reagents in immunoassays for Group A Strep, and typically contain a mixture of clones of variable affinity and specificity. Previous studies have reported that the addition of N-acetyl-D-glucosamine can improve assay specificity, thus reducing interference (false positives) caused by salivary proteins. However, this effect is accompanied by a significant reduction in assay sensitivity. See US 2013/0196337. A highly specific and sensitive immunoassay with a reduced rate of both false positives and false negatives is needed to provide accurate detection of Group A *Streptococcus* infection.

The present disclosure demonstrates that when N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine is included in the reagents of the lateral flow assay, it preferentially binds to the antibody clones that are less specific for the intact GAS antigen epitope, thus preventing those antibodies from cross-reacting with mucin and other glycoproteins. As demonstrated herein, the inclusion of N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine in lateral flow immunoassays eliminates or significantly reduces assay signal due to the presence of mucin, while retaining increased sensitivity for Group A Strep antigens.

Definitions

Unless otherwise defined, all technical and scientific terms used herein have the same meaning as commonly understood by one of ordinary skill in the art to which the present technology belongs.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed by this disclosure. The upper and lower limits of these smaller ranges may independently be included or excluded in the range, and each range where either, neither or both limits are included in the smaller ranges is also encompassed by this disclosure, subject to any specifically excluded limit in the stated range. Where the stated range includes one or both of the limits, ranges excluding either or both of those included limits are also within the scope of this disclosure.

As used herein, unless otherwise stated, the singular forms "a," "an," and "the" include plural references. Thus, for example, a reference to "a cell" includes a plurality of cells.

As used herein, the term "antibody" collectively refers to immunoglobulins or immunoglobulin-like molecules including by way of example and without limitation, IgA, IgD, IgE, IgG and IgM, combinations thereof, and similar molecules produced during an immune response in any vertebrate, for example, in mammals such as humans, goats, rabbits and mice, as well as non-mammalian species, such as shark immunoglobulins. As used herein, "antibodies" (includes intact immunoglobulins) and "antigen binding fragments" specifically bind to a molecule of interest (or a group of highly similar molecules of interest) to the substantial exclusion of binding to other molecules (for example, antibodies and antibody fragments that have a binding constant for the molecule of interest that is at least $10^3$ $M^{-1}$ greater, at least $10^4 M^{-1}$ greater or at least $10^5$ $M^{-1}$ greater than a binding constant for other molecules in a biological sample). The term "antibody" also includes genetically engineered forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, J., *Immunology,* 3rd Ed., W.H. Freeman & Co., New York, 1997.

More particularly, antibody refers to a polypeptide ligand comprising at least a light chain immunoglobulin variable region or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. Typically, an immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest,* U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds a target protein will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs) "Immunoglobulin-related compositions" as used herein, refers to antibodies (including monoclonal antibodies, polyclonal antibodies, humanized antibodies, chimeric antibodies, recombinant antibodies, multispecific antibodies, bispecific antibodies, etc.) as well as antibody fragments. An antibody or antigen binding fragment thereof specifically binds to an antigen.

The term "antigen binding fragment" refers to a fragment of the whole immunoglobulin structure which possesses a part of a polypeptide responsible for binding to antigen. Examples of the antigen binding fragment useful in the present technology include scFv, (scFv)$_2$, scFvFc, Fab, Fab' and F(ab')$_2$, but are not limited thereto.

As used herein, "associated" refers to coincidence with the development or manifestation of a disease, condition or phenotype. Association may be due to, but is not limited to, genes responsible for housekeeping functions whose alteration can provide the foundation for a variety of diseases and conditions, those that are part of a pathway that is involved in a specific disease, condition or phenotype and those that indirectly contribute to the manifestation of a disease, condition or phenotype.

By "binding affinity" is meant the strength of the total noncovalent interactions between a single binding site of a molecule (e.g., an antibody) and its binding partner (e.g., an antigen or antigenic peptide). The affinity of a molecule X for its partner Y can generally be represented by the dissociation constant ($K_D$). Affinity can be measured by standard methods known in the art, including those described herein. A low-affinity complex contains an antibody that generally tends to dissociate readily from the antigen, whereas a high-affinity complex contains an antibody that generally tends to remain bound to the antigen for a longer duration.

As used herein, "chromophore" refers to a moiety with absorption characteristics, i.e., are capable of excitation upon irradiation by any of a variety of photonic sources. Chromophores can be fluorescing or non-fluorescing, and include, among others, dyes, fluorophores, luminescent, chemiluminescent, and electrochemiluminescent molecules.

As used herein, the term "detecting" refers to determining the presence of a target polypeptide in the sample. Detection does not require the method to provide 100% sensitivity and/or 100% specificity.

As used herein, an "effective amount of N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine" refers to a quantity of N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine that is sufficient to preferentially bind to the antibody (or antigen binding fragment) clones that are less specific for the intact GAS antigen epitope, thus preventing those clones from cross-reacting with mucin and other glycoproteins.

As used herein, the term "epitope" means a protein determinant capable of specific binding to an antibody or an antigen binding fragment thereof. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. In some embodiments, the epitope is a conformational epitope or a non-conformational epitope.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same nucleobase or amino acid, then the molecules are homologous at that position. A degree of homology between sequences is a function of the number of matching or homologous positions shared by the sequences. A polynucleotide or polynucleotide region (or a polypeptide or polypeptide region) has a certain percentage (for example, at least 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art. In some embodiments, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the National Center for Biotechnology Information. Biologically equivalent polynucleotides are those having the specified percent homology and encoding a polypeptide having the same or similar biological activity. Two sequences are deemed "unrelated" or "non-homologous" if they share less than 40% identity, or less than 25% identity, with each other.

"Isolated antibody," as used herein, is intended to refer to an antibody which is substantially free of other antibodies having different antigenic specificities (e.g., an isolated antibody that specifically binds to the protein of interest is substantially free of antibodies that specifically bind antigens other than the protein of interest). An isolated antibody that specifically binds to an epitope, isoform or variant of the protein of interest may, however, have cross-reactivity to other related antigens, e.g., from other species (e.g., species homologs). Moreover, an isolated antibody may be substantially free of other cellular material and/or chemicals.

"Label" refers to any moiety that, when attached to a moiety described herein, e.g., a peptide, protein or antibody, renders such a moiety detectable using known detection methods, e.g., spectroscopic, photochemical, electrochemiluminescent, and electrophoretic methods. Various labels suitable for use in the present disclosure include labels which produce a signal through either chemical or physical means, wherein the signal is detectable by visual or instrumental means. Exemplary labels include, but are not limited to, gold nanoparticles, fluorophores and radioisotopes. Such labels allow direct detection of labeled compounds by a suitable detector, e.g., a fluorometer or a reflectance reader. Such labels can include enzymes and substrates, chromogens, catalysts, fluorescent compounds, phosphorescent compounds, chemiluminescent compounds, and radioactive labels. Typically, a visually detectable label is used, thereby providing for instrumental (e.g. spectrophotometer or a reflectance reader) readout of the amount of the analyte in the sample. Labels include enzymes such as horseradish peroxidase, galactosidase (alpha and/or beta), and alkaline phosphatase. Suitable substrates include 3,3',5,5'-tetramethylbenzidine (TMB) and 1,2 dioxetane. The method of detection will depend upon the labeled used, and will be apparent to those of skill in the art. Examples of suitable direct labels include gold nanoparticles, radiolabels, fluorophores, chromophores, chelating agents, particles, chemiluminescent agents and the like.

In some embodiments, the label is a direct label, i.e., a label that itself is detectable or produces a detectable signal, or an indirect label, i.e., a label that is detectable or produces a detectable signal in the presence of another compound. A "labeled second antibody" refers to an antibody that is attached to a detectable label. The label allows the antibody to produce a detectable signal that is related to the presence of analyte in the fluid sample. Examples of suitable radioactive labels include, but are not limited to, $^3H$, $^{14}C$, $^{32}P$, $^{35}S$, $^{36}Cl$, $^{57}Co$, $^{131}I$ and $^{186}Re$. Examples of suitable indirect labels include enzymes capable of reacting with or interacting with a substrate to produce a detectable signal (such as those used in enzyme-linked immunosorbent assay (ELISA) and Enzyme multiplied immunoassay technique (EMIT)), ligands capable of binding a labeled moiety, and the like. Suitable enzymes useful as indirect labels include, by way of example and not limitation, alkaline phosphatase, horseradish peroxidase, lysozyme, glucose-6-phosphate dehydrogenase, lactate dehydrogenase and urease. The use of these enzymes in ELISA and EMIT immunoassays is described in detail in Engvall, 1980, *Methods Enzym.* 70: 419-439 and U.S. Pat. No. 4,857,453.

The terms "protein," "polypeptide," "oligopeptide," and "peptide" are used interchangeably to refer to a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing (e.g., glycosylation, phosphorylation, lipidation, myristilation, ubiquitination, etc.), or by chemical modification techniques that are well known in the art.

The "positive predictive value (PPV)," or "precision rate" of a diagnostic test is a summary statistic used to describe the proportion of subjects with positive test results who are correctly diagnosed. It is a measure of the performance of a diagnostic method, as it reflects the probability that a positive test reflects the underlying condition being tested for. Its value does however depend on the prevalence of the outcome of interest, which may be unknown for a particular target population. The PPV can be derived using Bayes' theorem.

The PPV is defined as:

$$PPV = \frac{\text{\# of True Positives}}{(\text{\# of True Positives} + \text{\# of False Positives})} = \frac{\text{\# of True Positives}}{\text{\# of Positive calls}}$$

where a "true positive" is the event that the diagnostic test makes a positive prediction, and the subject has a positive result under the gold standard, and a "false positive" is the event that the test makes a positive prediction, and the subject has a positive result under the gold standard.

"Negative predictive value (NPV)" is defined as the proportion of subjects with a negative test result who are correctly diagnosed. A high NPV means that when the test yields a negative result, it is unlikely that the result should have been positive.

The NPV is determined as:

$$NPV = \frac{\text{\# of True Negatives}}{(\text{\# of True Negatives} + \text{\# of False Negatives})} = \frac{\text{\# of True Negatives}}{\text{\# of Negative calls}}$$

where a "true negative" is the event that the test makes a negative prediction, and the subject has a negative result under the gold standard, and a "false negative" is the event that the test makes a negative prediction, and the subject has a positive result under the gold standard.

If the prevalence, sensitivity, and specificity are known, the positive and negative predictive values (PPV and NPV) can be calculated for any prevalence as follows:

$$PPV = \frac{\text{sensitivity} \times \text{prevalence}}{\text{sensitivity} \times \text{prevalence} + (1 - \text{specificity}) \times (1 - \text{prevalence})}$$

$$NPV = \frac{\text{specificity} \times (1 - \text{prevalence})}{(1 - \text{sensitivity}) \times \text{prevalence} + \text{specificity} \times (1 - \text{prevalence})}$$

If the prevalence of the disease is very low, the positive predictive value will not be close to 1, even if both the sensitivity and specificity are high. Thus in screening the general population it is inevitable that many people with positive test results will be false positives. The rarer the abnormality, the higher the certainty that a negative test indicates no abnormality, and the lower the certainty that a positive result truly indicates an abnormality. The prevalence can be interpreted as the probability before the test is carried out that the subject has the disease, known as the prior probability of disease. The positive and negative predictive values are the revised estimates of the same probability for those subjects who are positive and negative on the test, and are known as posterior probabilities. The difference between the prior and posterior probabilities is one way of assessing the usefulness of the test.

For any test result, one can compare the probability of obtaining that result if the patient truly had the condition of interest with the corresponding probability if he or she were healthy. The ratio of these probabilities is called the likelihood ratio, calculated as sensitivity/(1-specificity). (Altman D G, Bland J M (1994). *BMJ* 309 (6947):102).

As used herein, the terms "individual", "patient", or "subject" can be an individual organism, a vertebrate, a mammal, or a human. In a preferred embodiment, the individual, patient or subject is a human.

The term "reference level" refers to a detected level of a positive or negative control. For example, a reference level of a positive control can be a known amount of Group A *Streptococcus*-specific antigen, obtained from a sample or culture of a known Group A *Streptococcus* bacterium, a subject known to be infected with Group A *Streptococcus*, or can refer to a numerical value derived from known sources of Group A *Streptococcus*-specific antigen.

As used herein, the term "sample" refers to clinical samples obtained from a patient or isolated microorganisms.

In preferred embodiments, a sample is obtained from a biological source (i.e., a "biological sample"), such as tissue, bodily fluid, or microorganisms collected from a subject. Sample sources include, but are not limited to, mucus, sputum (processed or unprocessed), bronchial alveolar lavage (BAL), bronchial wash (BW), blood, bodily fluids, cerebrospinal fluid (CSF), urine, plasma, serum, or tissue (e.g., biopsy material). Preferred sample sources include nasopharyngeal and/or throat swabs or nasal washes. As pertains to the present disclosure, a biological fluid can be a solid, or semi-solid sample, including feces, biopsy specimens, skin, nails, and hair, or a liquid sample, such as urine, saliva, sputum, mucous, a throat swab sample, blood, blood components such as plasma or serum, amniotic fluid, semen, vaginal secretions, tears, spinal fluid, washings, and other bodily fluids. Included among the sample are swab specimens from, e.g., the cervix, urethra, nostril, and throat. Any of such samples may be from a living, dead, or dying animal or a plant.

In statistics and diagnostic testing, sensitivity and specificity are statistical measures of the performance of a binary classification test. "Sensitivity" (also called "recall rate") measures the proportion of actual positives which are correctly identified as such (e.g. the percentage of subjects who are correctly identified as having a condition). Sensitivity relates to the ability of a diagnostic test to identify positive results and is computed as the number of true positives divided by the sum of the number of true positives and the number of false negatives. "Specificity" measures the proportion of negatives which are correctly identified (e.g., the percentage of healthy subjects who are correctly identified as not having the condition). Specificity relates to the ability of a diagnostic test to identify negative results and is computed as the number of true negatives divided by the sum of the number of true negatives and the number of false positives. Sensitivity and specificity are closely related to the concepts of type I and type II errors. A theoretical, optimal prediction aims to achieve 100% sensitivity and 100% specificity, however theoretically any predictor will possess a minimum error bound known as the Bayes error rate.

For any test, there is usually a trade-off between sensitivity and specificity, which can be represented graphically using a receiver operating characteristic (ROC) curve. In some embodiments, a ROC is used to generate a summary statistic. Some common versions are: the intercept of the ROC curve with the line at 90 degrees to the no-discrimination line (also called Youden's J statistic); the area between the ROC curve and the no-discrimination line; the area under the ROC curve, or "AUC" ("Area Under Curve"), or A' (pronounced "a-prime"); d' (pronounced "d-prime"), the distance between the mean of the distribution of activity in the system under noise-alone conditions and its distribution under signal-alone conditions, divided by their standard deviation, under the assumption that both these distributions are normal with the same standard deviation. Under these assumptions, it can be proved that the shape of the ROC depends only on d'.

"Rule-out criteria" "Rule-Out," or "RO" are terms used in a medical differential diagnosis of a disease or condition, in which certain criteria are evaluated in a clinical decision-making process of elimination or inclusion. A subject is "ruled-out" when, upon consideration of the criteria, the subject has been determined not to have met all or a significant number of criteria for having a disease.

As used herein, "specifically binds" refers to a molecule (e.g., an antibody or antigen binding fragment thereof) which recognizes and binds another molecule (e.g., an antigen), but that does not substantially recognize and bind other molecules. The terms "specific binding," "specifically binds to," or is "specific for" a particular molecule (e.g., a polypeptide, or an epitope on a polypeptide), as used herein, can be exhibited, for example, by a molecule having a $K_D$ for the molecule to which it binds to of about $10^{-4}$ M, $10^{-5}$M, $10^{-6}$M, $10^{-7}$ M, $10^{-8}$ M, $10^{-9}$ M, $10^{-10}$ M, $10^{-11}$M, or $10^{-12}$M. The term "specifically binds" may also refer to binding where a molecule (e.g., an antibody or antigen binding fragment thereof) binds to a particular polypeptide (e.g., a target polypeptide), or an epitope on a particular polypeptide, without substantially binding to any other polypeptide, or polypeptide epitope.

"Substrate," "support," "solid support," "solid carrier," or "resin" are interchangeable terms and refer to any solid phase material. Substrate also encompasses terms such as "solid phase," "surface," and/or "membrane." A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. "Solid support" includes membranes (e.g. nitrocellulose), microtiter plate (e.g. PVC, polypropylene, polystyrene), dipstick, test tube, and glass or plastic beads. The configuration of a substrate can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location. A plurality of supports can be configured on an array at various locations, addressable for robotic delivery of reagents, or by detection methods and/or instruments. Methods for immobilizing biomolecules are well known in the art, and the antibody can be attached covalently or non-covalently to a substrate. In certain embodiments, the solid support is a streptavidin coated plate to which a biotinylated antibody is non-covalently attached.

Diagnostic Methods of the Present Technology

In one aspect, the present disclosure provides a method for detecting the presence of at least one Group A *Streptococcus* species in a biological sample comprising: (a) contacting the biological sample with an antibody or an antigen binding fragment that specifically targets a Group A *Streptococcus*-specific antigen and an effective amount of N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine; and (b) detecting binding of the antibody or the antigen binding fragment to the Group A *Streptococcus*-specific antigen, if present, in the sample, wherein detection of binding of the antibody or the antigen binding fragment to the Group A *Streptococcus*-specific antigen indicates the presence of at least one Group A *Streptococcus* species in the sample.

Examples of the antibodies or antigen binding fragments used in the immunoassay of the present disclosure may include, but are not limited to a polyclonal antibody, such as an affinity purified rabbit anti-Strep A antibody. Illustrative publications describing components of precursor compositions, methods and kits, as well as various antibodies for detecting Group A *Streptococcus* include the following: U.S. Pat. Nos. 5,415,994; 5,763,262 and 5,770,460. All of these patents, applications and publications are incorporated by reference herein, in their entirety. In some embodiments, the antibody is a polyclonal antibody. In some embodiments, the antibody is a monoclonal antibody. In some embodiments, the antibody or antigen binding fragment binds to one or more epitopes of Group A *Streptococcus*, and also binds to N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine. In some embodiments, the antibody is a population of polyclonal antibodies, the population including a portion of antibodies having specific binding to N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine. In some embodiments, the antibody or antigen binding fragment does not bind to glucosamine, galactosamine, mannosamine, acetyl-muramic acid, chitin, chitosan, and/or hyaluronic acid (e.g., HA-50K).

In some embodiments, the antibody or antigen binding fragment has high specificity and low sensitivity for detecting a Group A *Streptococcus* antigen. In some embodiments, the antibody or antigen binding fragment has high sensitivity and low specificity for detecting a Group A *Streptococcus* antigen. In some embodiments, the antibody or antigen binding fragment has high specificity and high sensitivity for detecting a Group A *Streptococcus* antigen.

Additionally or alternatively, in some embodiments, the Group A *Streptococcus*-specific antigen may be selected from the group consisting of capsular polysaccharide ("C-substance"), cell wall peptidoglycan, lipoteichoic acid (LTA), M protein, fimbrial proteins, fibronectin-binding proteins, and cell-bound streptokinase. Examples of Group A *Streptococcus* species include *Streptococcus pyogenes* or *Streptococcus dysgalactiae*.

Additionally or alternatively, in some embodiments, the antibody or antigen binding fragment comprises a gold nanoparticle label, a chemiluminescent label, a radioactive label, a bioluminescent label, a fluorescent label, a chromogenic label (e.g., gold nanoparticles), a spectroscopic label, a photochemical label, or an electrochemiluminescent label. Examples of fluorescent labels include, but are not limited to, europium, TagBFP, Azurite, EBFP2, mKalama1, Sirius, Sapphire, T-Sapphire, ECFP, Cerulean, SCFP3A, mTurquoise, monomeric Midoriishi-Cyan, TagCFP, mTFP1, EGFP, Emerald, Superfolder GFP, Monomeric Azami Green, TagGFP2, mUKG, mWasabi, EYFP, Citrine, Venus, SYFP2, TagYFP, Monomeric Kusabira-Orange, mKOK, mKO2, mOrange, mOrange2, mRaspberry, mCherry, dsRed, mStrawberry, mTangerine, tdTomato, TagRFP, TagRFP-T, mApple, mRuby, mPlum, HcRed-Tandem, mKate2, mNeptune, NirFP, TagRFP657, IFP1.4, iRFP, mKeima Red, LSS-mKate1, LSS-mKate2, PA-GFP, PAmCherry1, PATagRFP, Kaede (green), Kaede (red), KikGR1 (green), KikGR1 (red), PS-CFP2, PS-CFP2, mEos2 (green), mEos2 (red), PSmOrange, and Dronpa. Examples of chemiluminescent labels include, but are not limited to, β-galactosidase, horseradish peroxidase (HRP), and alkaline phosphatase. Examples of bioluminescent labels include aequorin, firefly luciferase, *Renilla* luciferase, red luciferase, luxAB, or nanoluciferase. Examples of radioactive labels include 3H, $^{14}$C, $^{32}$P, $^{35}$S, $^{36}$Cl, $^{57}$Co, $^{131}$I and $^{186}$Re.

In some embodiments of the methods disclosed herein, the biological sample is a body fluid, such as urine, saliva, sputum, mucous, a throat swab sample, blood, blood components such as plasma or serum, amniotic fluid, semen, wound secretions, vaginal secretions, tears, spinal fluid, washings, and other bodily fluids. Biological samples include swab specimens from, e.g., the cervix, urethra, nostril, and throat. In some embodiments, the biological sample is collected through the use of a pharyngeal swab. In some embodiments, the biological sample is collected through a swab of the pharynx, tongue, cheek, teeth, gums or nasal passages.

Additionally or alternatively, in some embodiments of the methods of the present technology, binding of the antibody or the antigen binding fragment to the Group A *Streptococcus*-specific antigen is detected via enzyme-linked immunosorbent assay (ELISA) or Enzyme multiplied immunoassay technique (EMIT).

Additionally or alternatively, in some embodiments, the biological sample is obtained from a subject suffering from or suspected of having a bacterial infection. In certain embodiments, the subject is human.

Without being bound to a particular theory, the data demonstrates that the false positive signals from glycoproteins present in epithelial cells inadvertently collected on oral swab specimens can be efficiently blocked or suppressed by addition of N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine to the immunoassay, without compromising the overall sensitivity and/or PPV of the assay. The polyclonal or monoclonal anti-Strep A antibodies used in the immunoassay may, in some embodiments, include a population of antibodies that recognize human epithelial cell wall glycoproteins that mimic Group A streptococcal cell wall proteins. By providing a reagent to the immunoassay that can block this population of antibodies, the performance of the immunoassay in terms of overall accuracy by reducing the rate of false positives can be improved. The results also demonstrate that unlike NAG, the addition of N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine reduces the overall false negative rate of the immunoassay. In some embodiments, the NPV of the immunoassay is improved compared to that observed in the absence of N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine.

Figure 12:
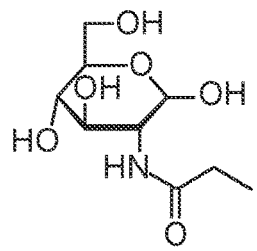
FIG. 12 shows the structures of the N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, and m-PEG10-glucosamine compositions disclosed herein.
Figure 12:
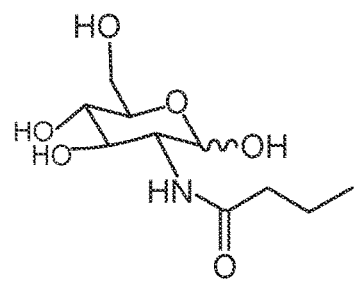
Figure 12:
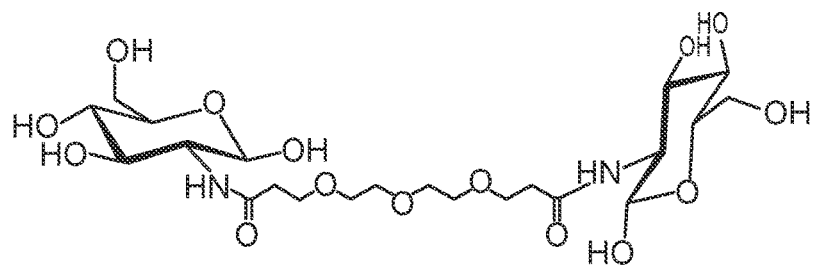
Figure 12:
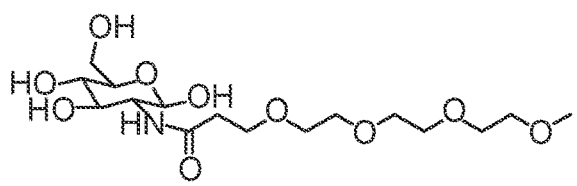
Figure 12:
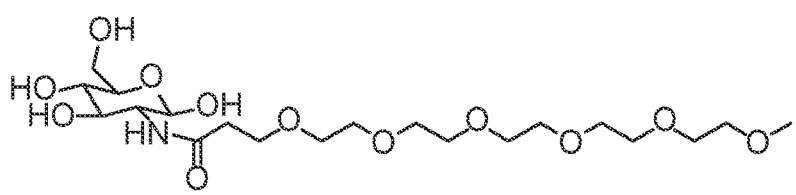
Figure 12:
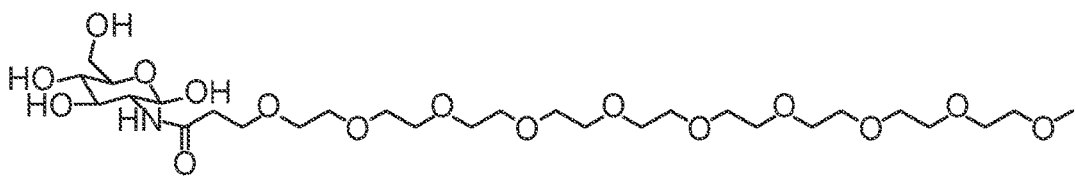

Accordingly, in some embodiments, the addition of N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine to an immunoassay is contemplated, where the presence of N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine is effective to reduce non-specific binding between the antibodies in the Strep A polyclonal antibody population and components in the test sample by at least about 50%, more preferably by at least about 60%, at least about 65%, at least about 70%, at least about 75%, at least about 80%, at least about 85%, at least about 90%, at least about 95%, at least about 96%, at least about 97%, at least about 98%, at least about 99% of the signal obtained in the absence of N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine Immunoassay Devices of the Present Technology Immunoassays for detection of Group A *Streptococcus* that comprise N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine (see FIG. 12) are contemplated, wherein the assay comprises a lateral flow device that allows for pretreatment and detection of Group A *Streptococcus* organisms with enhanced specificity. Immunoassay devices are known in the art, and typically have at least a sample receiving zone, a labeling zone and a capture zone, and can be prepared according to the description in any of U.S. Pat. Nos. 5,415,994; 5,763,262 and 5,770,460, and U.S. Pat. Application Publication No. 20090305231, which are incorporated by reference in their entirety.

Accordingly, in one aspect of the disclosure, a device is provided for detecting the presence of Group A *Streptococcus* in a sample. Various embodiments of a device are contemplated, and exemplary embodiments are described herein for the purposes of illustration. A skilled artisan will appreciate, however, that the illustrative embodiments are non-limiting to the inventive concepts set forth herein.

In a general embodiment, a device comprises a series of zones in fluid communication. In certain embodiments, a sample receiving zone is in fluid communication with second and subsequent zones, such as a labeling zone, a capture zone, and/or an absorption zone.

One particular embodiment of the device of the present technology includes an immunoassay test strip for detection of Group A *Streptococcus*. An exemplary test strip is comprised of a support layer that optionally extends the length of the test strip. The support layer supports in series a sample pad, a label pad (which may include a conjugate pad where the antibodies or antigen binding fragments are conjugated to a label), a nitrocellulose member, and an optional absorbent pad. On the nitrocellulose member is a test line and a control line. For detection of Strep A, the label pad comprises anti-Strep A antibodies, as does the test line. In one embodiment, the antibodies or antigen binding fragments deposited on the label pad are detector antibodies or detector antigen binding fragments that comprise a label which aids or permits detection of the antibody or antigen binding fragments. The labeled antibody or antigen binding fragment specifically binds the Strep A antigen as it passes through the label zone. The capture zone comprises a means for specifically binding the labeled antigen thereon. In some embodiments, the sample is contacted with N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine prior to application to the device and/or during its flow through the device. Studies described herein illustrate the improved performance of a device intended for detecting Strep A when N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine is incorporated in the assay. N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine can be incorporated into the device, such as in the sample receiving zone, the labeling zone, the capture zone, or any combination thereof, and/or the sample can be treated with N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine prior to its application to the sample receiving zone of device.

In one embodiment, the lateral flow immunoassay comprises an immunoassay with a detector label that can be read visually with the unaided eye, such as a colored bead or particle, wherein a collection of such beads or particles at the test line of the immunoassay can be viewed by a user with the naked eye. In another embodiment, the lateral flow immunoassay comprises an immunoassay with a label that is read by an instrument or by an eye with the aid of an instrument. For example, a fluorescent, chemiluminescent, bioluminescent, gold nanoparticle, or radioactive label in the immunoassay is detected using an instrument such as, for example, a reflectance reader or a fluorescence detector. An exemplary instrument and lateral flow immunoassay is described in U.S. Application No. 61/666,689 and U.S. Pat. No. 9,207,181, which are incorporated by reference herein. Another exemplary instrument and lateral flow immunoassay is described in U.S. application Ser. No. 12/420,574, which is incorporated by reference herein.

In another aspect, a device is provided for detecting the presence of Group A *Streptococcus* in a sample, wherein the device comprises a matrix having (i) a sample receiving zone for receiving a sample containing or suspected of containing a Group A *Streptococcus*-specific antigen, (ii) a labeling zone containing a detector antibody for specifically labeling the antigen as it passes there through and (iii) a capture zone having means for specifically binding the labeled antigen thereon, wherein the sample receiving zone, the labeling zone and the capture zone are arranged on the matrix in a liquid flow path, and wherein the sample receiving zone, the labeling zone, the capture zone, or any combination thereof contains N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine.

Another embodiment of a device contemplated for use is described in U.S. Pat. No. 5,415,994, which is incorporated by reference herein. In this embodiment, the device comprises a receiving chamber positioned or positionable for fluid contact with a lateral flow immunoassay device, and preferably positioned for fluid communication with a sample receiving zone or a labeling zone of the immunoassay test strip. The biological sample suspected of containing Strep A is received into the receiving chamber, such as by insertion of a swab containing the sample or by dispensing an aliquot of the sample into the receiving chamber. One or more extraction or treatment agents can be additionally added to the receiving chamber or to the swab. In some embodiments, the treatment agent comprises N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine. In certain embodiments, the receiving chamber is positioned over the sample receiving zone that is dimensioned for receiving a liquid extraction reagent comprising N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine, and, optionally comprises a cylindrical portion for receiving a swab containing a patient sample. The immunoassay test strip comprises a matrix having a sample receiving zone for receiving the extraction liquid containing the treated sample suspected of comprising Strep A antigen, a labeling zone having a detector antibody or detector antigen binding fragment for specifically labeling the antigen as it passes there through and a capture zone having means for specifically binding the labeled antigen thereon, wherein the sample receiving zone, the labeling zone, and the capture zone are arranged on the matrix in a liquid flow path. In some embodiments, the detector antibody is polyclonal. In some embodiments, the detector antibody is a monoclonal antibody.

In some embodiments of the devices described herein, the extraction reagent provided to treat the biological sample comprises N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine. In some embodiments, the labeling zone of the immunoassay device includes N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine. In certain embodiments, the capture zone of the immunoassay device comprises N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine. In some embodiments, the sample receiving zone of the immunoassay device includes N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine. In some embodiments, all or some of these specified zones comprises N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine in an extraction reagent.

In another aspect, the present disclosure provides a method for detecting the presence of Strep A in a biological sample, comprising (a) providing a matrix having (i) a sample receiving zone for receiving a sample containing or suspected of containing a Group A *Streptococcus*-specific antigen, (ii) a labeling zone containing a detector antibody or detector antigen binding fragment for specifically labeling the antigen as it passes there through and (iii) a capture zone having means for specifically binding the labeled antigen thereon, wherein the sample receiving zone, the labeling zone and the capture zone are arranged on the matrix in a liquid flow path, and (b) contacting the sample receiving zone with the sample, wherein said sample is pre-treated with a liquid reagent comprising N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine; and (c) detecting the presence of the antigen in the capture zone. In some embodiments, the matrix additionally comprises an absorbent zone downstream of the capture zone.

In another aspect, the present disclosure provides a method to reduce the false positive rate of a lateral flow assay in the detection of Group A *Streptococcus* in a liquid sample, wherein, in the lateral flow assay, N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine-binding components of a polyclonal antibody (or antigen binding fragment) label used in the assay are preferentially bound, the method comprising treating a bibulous matrix with an amount of N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine effective as a blocking agent to enhance the specific binding of the polyclonal antibody (or antigen binding fragment) to Strep A antigen and reduce the false positive rate of the assay.

In another aspect, the present disclosure provides a method to reduce the false positive rate of a lateral flow assay in the detection of Group A *Streptococcus* in a liquid sample, wherein, in the lateral flow assay, N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine-binding components of a polyclonal antibody (or antigen binding fragment) label used in the assay are preferentially bound, the method comprising adding to an extraction reagent an amount of N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine effective as a blocking agent to enhance the specific binding of the polyclonal antibody (or antigen binding fragment) to Strep A antigen and reduce the false positive rate of the assay.

Improvements to a known immunoassay device for detecting Group A *Streptococcus* can be made by adding N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine to the sample receiving zone in an amount effective as a blocking agent to enhance the specific binding of at least a portion of the polyclonal antibodies to Strep A antigen, to thereby reduce the false positive rate of the assay. Improvements can also comprise adding N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine to the labeling zone in an amount effective as a blocking agent to enhance the specific binding of the polyclonal antibody to Strep A antigen and reduce the false positive rate of the assay. Improvements can also comprise adding N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine to the extraction reagent in an amount effective as a blocking agent to enhance the specific binding of the polyclonal antibody to Strep A antigen and reduce the false positive rate of the assay. Improvements can also comprise adding N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine to the capture line in an amount effective as a blocking agent to enhance the specific binding of the polyclonal antibody to Strep A antigen and reduce the false positive rate of the assay.

Treatment Selection Methods of the Present Technology

In another aspect, the present disclosure provides methods for selecting a patient for antibiotic therapy. In some embodiments, the method comprises detecting the presence of at least one Group A *Streptococcus* species in a biological sample obtained from the patient using any of the devices disclosed herein; and administering antibiotic therapy to the patient. In other embodiments, the method comprises (a) contacting a biological sample obtained from the patient with an antibody or an antigen binding fragment that specifically targets a Group A *Streptococcus*-specific antigen and an effective amount of N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine; and (b) administering antibiotic therapy to the patient when binding between the antibody or antigen binding fragment and the Group A Streptococcus-specific antigen is detected in the sample. In some embodiments of the methods disclosed herein, the antibiotic therapy comprises one or more of penicillin, ampicillin, sulbactam, amoxicillin, clavulanic acid, clindamycin, erythromycin, macrolides, and cephalosporins. In some embodiments, the macrolide-antibiotics are selected from the group consisting of azithromycin (Zithromax), clarithromycin (Biaxin), erythromycin (E-Mycin, Eryc, Ery-Tab, PCE, Pediazole, Ilosone), and roxithromycin. Examples of cephalosporins include Cefacetrile (e.g., cephacetrile), Cefadroxil (e.g., cefadroxyl; Duricef), Cefalexin (e.g., cephalexin; Keflex), Cefaloglycin (e.g., cephaloglycin), Cefalonium (e.g., cephalonium), Cefaloridine (e.g., cephaloradine), Cefalotin (e.g., cephalothin; Keflin), Cefapirin (e.g., cephapirin; Cefadryl), Cefatrizine, Cefazaflur, Cefazedone, Cefazolin (e.g., cephazolin; Ancef, Kefzol), Cefradine (e.g., cephradine; Velosef), Cefroxadine, Ceftezole, Cefaclor (e.g., Ceclor, Distaclor, Keflor, Raniclor), Cefonicid (e.g., Monocid), Cefprozil (e.g., cefproxil; Cefzil), Cefuroxime (e.g., Zefu, Zinnat, Zinacef, Ceftin, Biofuroksym, Xorimax), Cefuzonam, Cefmetazole, Cefotetan, Cefoxitin, Loracarbef (e.g., Lorabid), Cefbuperazone, Cefmetazole (e.g., Zefazone), Cefminox, Cefotetan (e.g., Cefotan), Cefoxitin (e.g., Mefoxin), Cefotiam (e.g., Pansporin), Cefcapene, Cefdaloxime, Cefdinir (e.g., Sefdin, Zinir, Omnicef, Kefnir), Cefditoren, Cefetamet, Cefixime (e.g., Fixx, Zifi, Suprax), Cefmenoxime, Cefodizime, Cefotaxime (e.g., Claforan), Cefovecin (e.g., Convenia), Cefpimizole, Cefpodoxime (e.g., Vantin, PECEF, Simplicef), Cefteram, Ceftamere (e.g., Enshort), Ceftibuten (e.g., Cedax), Ceftiofur (e.g., Naxcel, Excenel), Ceftiolene, Ceftizoxime (e.g., Cefizox), Ceftriaxone (e.g., Rocephin), Cefoperazone (e.g., Cefobid), Ceftazidime (e.g., Meezat, Fortum, Fortaz), Latamoxef (e.g., moxalactam), Cefclidine, Cefepime (e.g., Maxipime), Cefluprenam, Cefoselis, Cefozopran, Cefpirome (e.g., Cefrom), Cefquinome, Flomoxef, Ceftobiprole, Ceftaroline, Ceftolozane, Cefaloram, Cefaparole, Cefcanel, Cefedrolor, Cefempidone, Cefetrizole, Cefivitril, Cefmatilen, Cefmepidium, Cefoxazole, Cefrotil, Cefsumide, Ceftioxide, Cefuracetime, and Nitrocefin.

Kits

The present disclosure also provides kits for detecting target epitopes corresponding to Group A Streptococcus species, comprising detector antibodies (or detector antigen binding fragments thereof) that target Group A Streptococcus-specific antigens, at least one of N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine, and instructions for use. The detector antibodies may be polyclonal antibodies or monoclonal antibodies. In a specific embodiment, the detector antibodies are polyclonal antibodies. Additionally or alternatively, in some embodiments, the kits comprise an immunoassay device as described herein. In addition to the immunoassay device, the kits may additionally include any one or more of: written instructions for using the device and collecting a biological sample, an instrument or tool for collecting a biological sample, labels for marking the device, a container or vial containing an extraction reagent for treating a collected sample, and a container or vial containing a reagent for preparing a treated sample. The kits may optionally include instructions for reading and interpreting the results of an assay. The kits may further comprise reference samples that may be used to compare test results with the specimen samples. In certain embodiments, the kits include a swab for collecting a biological sample, a container or vial containing an extraction reagent for treating a collected biological sample, and instructions for use of the assay and for collecting the sample, wherein the instructions do not contain a caution against contacting, for example, one or more of the back of the throat, tonsils, cheek or tongue.

In another aspect, the present disclosure provides a kit comprising (a) a device including a matrix having (i) a sample receiving zone for receiving a sample containing or suspected of containing a Group A Streptococcus-specific antigen, (ii) a labeling zone containing a detector antibody (or detector antigen binding fragments thereof) for specifically labeling the antigen as it passes there through and (iii) a capture zone having means for specifically binding the labeled antigen thereon, and, optionally (iv) an absorbent zone, wherein the sample receiving zone, the labeling zone, and the capture zone (and the optional absorbent if present) are arranged on the matrix in a liquid flow path; and (b) a container comprising an extraction reagent; wherein at least one of the extraction reagent, the sample receiving zone, the capture zone, and the labeling zone contain N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine.

Additionally or alternatively, in some embodiments, the kit comprises a lateral flow immunoassay test strip housed in a cassette with a sample receiving chamber, wherein the test strip includes a sample pad comprising N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine. The N-propionyl-D-glucosamine, 2-N-butanoyl-D-glucosamide, Bis-(2-(D-2-deoxy-glucosaminyl))-PEG3-amide, m-PEG4-glucosamine, m-PEG6-glucosamine, or m-PEG10-glucosamine may be in dried form. Additionally or alternatively, in some embodiments, the kit further comprises one or more of a vial with a reagent solution, a dropper tip that fits securely on the open end of the vial, a sterile rayon swab, a positive control swab (e.g., coated with heat-inactivated, non-infectious Group A Streptococcus), a negative control swab (e.g., coated with heat-inactivated, non-infectious Group C Streptococcus), and instructions for use. The test strip may be designed to work in conjunction with an instrument capable or reading reflectance or a fluorescent or luminescent signal emitted from a test line and a control line on the test strip.

The kit may further comprise one or more of: wash buffers and/or reagents, hybridization buffers and/or reagents, labeling buffers and/or reagents, and detection means. The buffers and/or reagents are usually optimized for the particular amplification/detection technique for which the kit is intended. Protocols for using these buffers and reagents for performing different steps of the procedure may also be included in the kit.

EXAMPLES

Example 1: Inclusion of
N-Propionyl-D-Glucosamine Reduces False
Positive and False Negative Signals in Strep A
Lateral Flow Immunoassay Saliva samples were collected from four asymptomatic patients and tested with an immunoassay test strip for specificity. Previous studies have reported that samples obtained from the mouth tissues, saliva, cheek and tongue of healthy control patients show high false positive rates for Strep A when assayed via a lateral flow immunoassay. See US20130196337A1.

N-propionyl-D-glucosamine was tested for its ability to inhibit or block the binding of the anti-Strep A polyclonal antibodies in the Strep A immunoassay. Saliva samples from four asymptomatic patients were obtained for testing. Using an immunoassay device for detection of Strep A, the four saliva samples were each treated with the extraction reagents (such as the extraction reagents in a commercially available BD Veritor™ Strep A kit) in the presence of N-propionyl-D-glucosamine, which was dried on the conjugate pad during the spraying of liquid conjugate on the conjugate pad (labeling zone). Different concentrations of N-propionyl-D-glucosamine in an immunoassay were evaluated for inhibition of Strep A false positive signals.

As shown in FIGS. 1-4, false positive signals from saliva specimens were efficiently suppressed by addition of N-propionyl-D-glucosamine demonstrating that cross-reactivity between Strep A polyclonal antibodies and human tissue or cells from oral cavities was effectively suppressed. Moreover, the addition of N-propionyl-D-glucosamine did not reduce the overall sensitivity of the Veritor™ Strep A assay. See FIG. 1 and FIG. 3.

These results demonstrate that addition of N-propionyl-D-glucosamine to an immunoassay for Strep A improves the specificity of the test for Group A *Streptococcus*, and unlike NAG, reduces the rate of false negatives. Thus, N-propionyl-D-glucosamine can be used to effectively reduce false positives and false negatives in such tests. A skilled artisan will appreciate that the amount of antibody, N-propionyl-D-glucosamine and sample can be adjusted for optimization of observing a positive signal from *S. pyogenes* while blocking false positives by N-propionyl-D-glucosamine.

These results demonstrate that the compositions and devices disclosed here are useful in methods for detecting the presence of at least one Group A *Streptococcus* species in a biological sample.

Example 2: Inclusion of 2-N-Butanoyl-D-Glucosamide, or Bis-(2-(D-2-Deoxy-Glucosaminyl))-PEG3-Amide Reduces False Positive and False Negative Signals in Strep A Lateral Flow Immunoassay 2-N-butanoyl-D-glucosamide, or Bis-(2-(D-2-deoxy-glucosaminyl))-PEG3-amide were tested for their ability to inhibit or block the binding of the anti-Strep A polyclonal antibodies in the Strep A immunoassay (Veritor™ Strep A assay). Porcine mucin samples were used as a surrogate of human saliva sample, and were tested with an immunoassay test strip for specificity. Using an immunoassay device for detection of Strep A, the effect of 2-N-butanoyl-D-glucosamide, or Bis-(2-(D-2-deoxy-glucosaminyl))-PEG3-amide on the performance of Strep A assay was evaluated using 4× concentration of mucin standard (~2.5 mg/mL) and Test Standard 1. Either 2-N-butanoyl-D-glucosamide, or Bis-(2-(D-2-deoxy-glucosaminyl))-PEG3-amide was added directly to the sample. Different concentrations of 2-N-butanoyl-D-glucosamide, or Bis-(2-(D-2-deoxy-glucosaminyl))-PEG3-amide in an immunoassay were evaluated for inhibition of Strep A false positive signals.

Figure 5A:
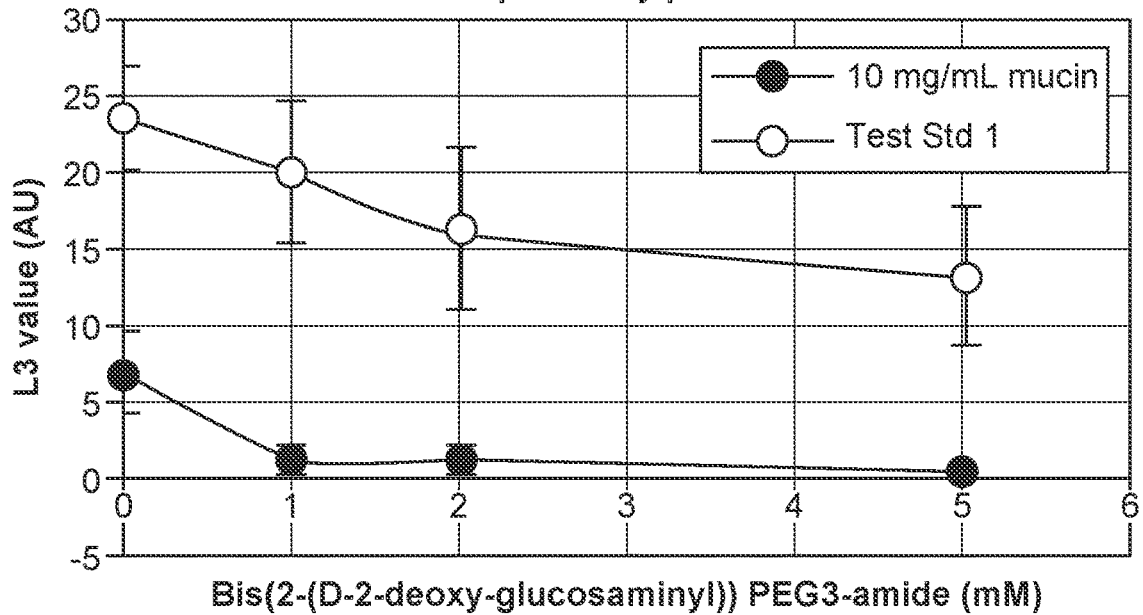
FIGS. 5A-5B show the effect of Bis-(2-(D-2-deoxy-glucosaminyl))-PEG3-amide on the sensitivity and specificity of the Veritor™ Strep A assay. In this experiment, different concentrations of Bis-(2-(D-2-deoxy-glucosaminyl))-PEG3-amide were mixed with either a sample containing Strep A antigen or a mucin sample before they were added to the sample well of a lateral flow test device.
Figure 5B:
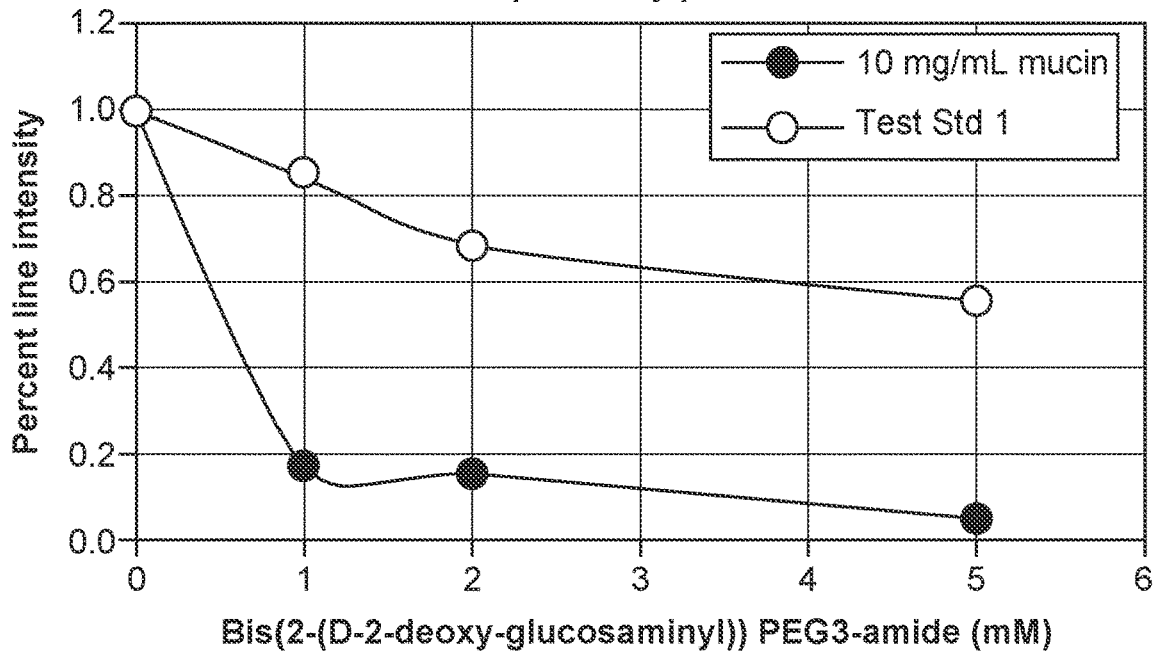
Figure 6:
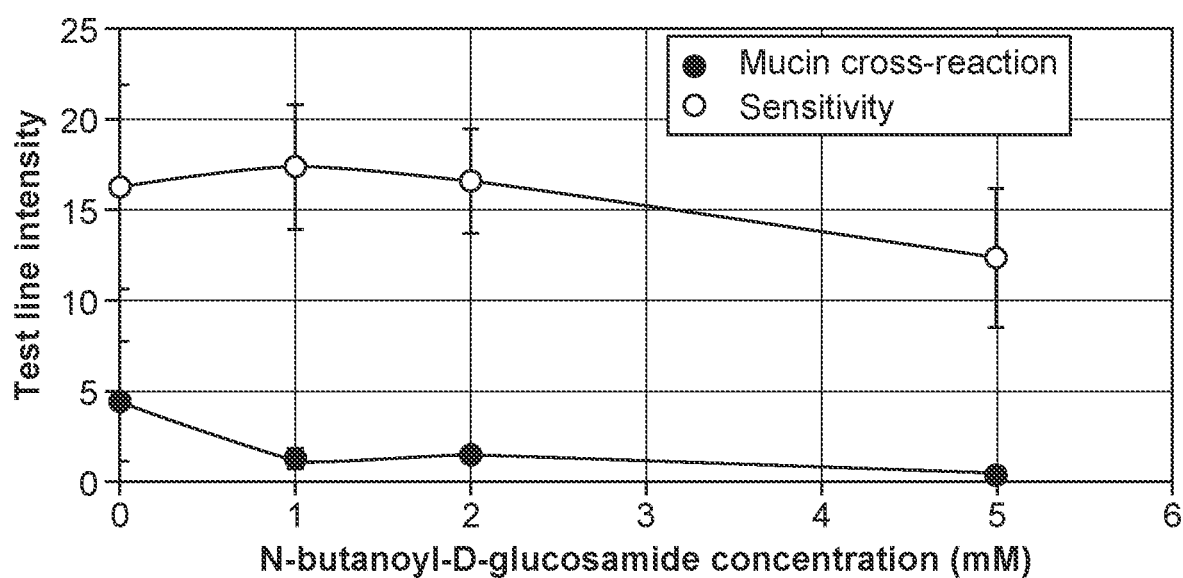
FIG. 6 shows the effect of 2-N-butanoyl-D-glucosamide on the sensitivity and specificity of the Veritor™ Strep A assay. In this experiment, different concentrations of 2-N-butanoyl-D-glucosamide were mixed with either a sample containing Strep A antigen or a mucin sample before they were added to the sample well of a lateral flow test device.

As shown in FIGS. 5-6, false positive signals from porcine mucin samples were efficiently suppressed by addition of 2-N-butanoyl-D-glucosamide, or Bis-(2-(D-2-deoxy-glucosaminyl))-PEG3-amide demonstrating that cross-reactivity between Strep A polyclonal antibodies and mucins was effectively suppressed. Moreover, the addition of 2-N-butanoyl-D-glucosamide, or Bis-(2-(D-2-deoxy-glucosaminyl))-PEG3-amide did not significantly reduce the overall sensitivity of the Veritor™ Strep A assay.

Figure 7:
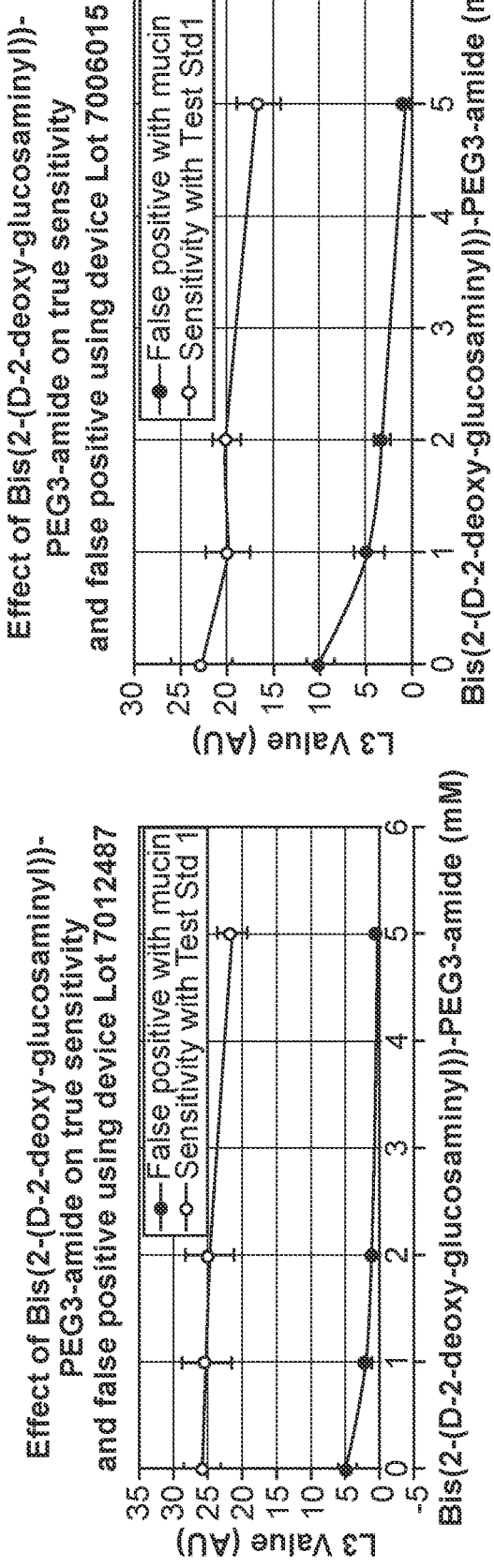
FIG. 7 shows the effect of the dimer Bis(2-(D-2-deoxy-glucosaminyl))-PEG3-amide added in a sample on the performance of two lots of Strep A devices that previously showed mucin cross-reaction. In this experiment, different concentrations of Bis-(2-(D-2-deoxy-glucosaminyl))-PEG3-amide were mixed with either a sample containing Strep A antigen or a mucin sample before they were added to the sample well of a lateral flow test device.
Figure 7:
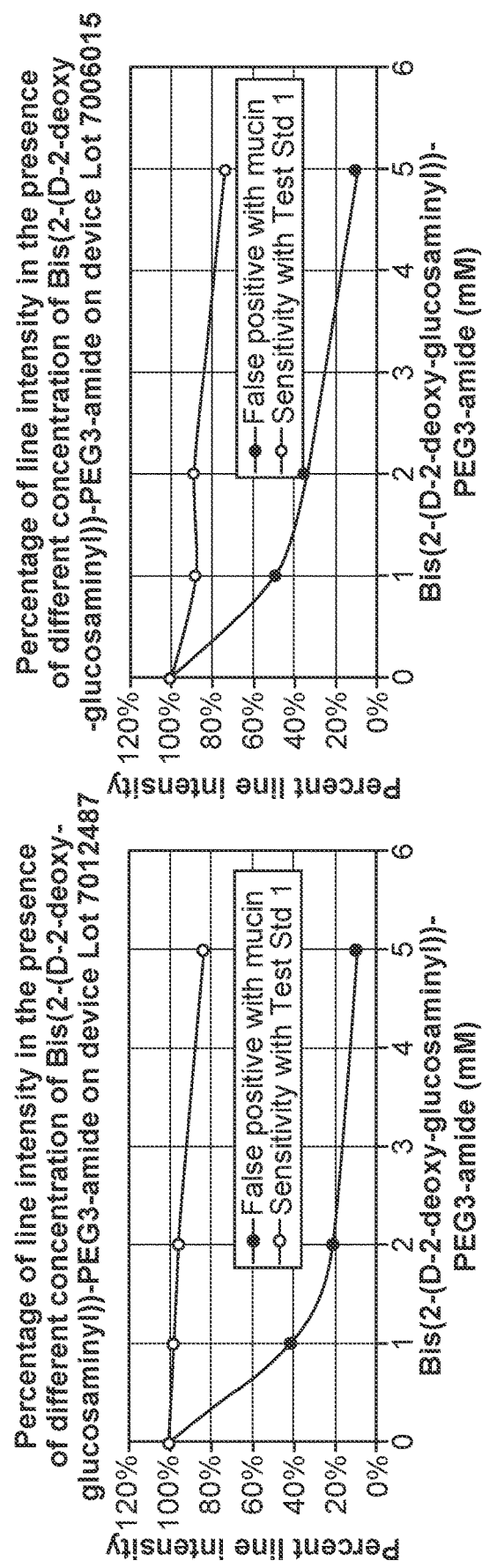

FIG. 7 shows the effect of Bis(2-(D-2-deoxy-glucosaminyl))-PEG3-amide added in a sample on the performance of two lots of Strep A devices that previously showed mucin cross-reaction. The dimer slightly inhibited true sensitivity, while significantly reducing mucin induced false positive signal.

Figure 8:
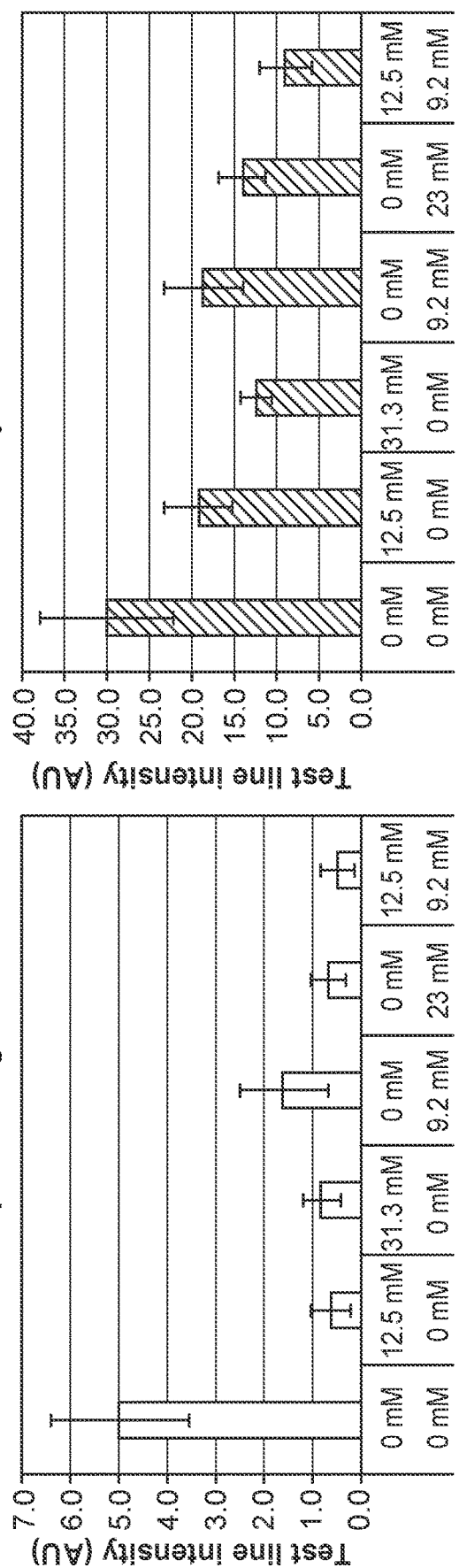
FIG. 8 shows the effect of adding Bis(2-(D-2-deoxyl-glucosaminyl)-PEG3-amide to the conjugate pad and sample pad dipping solution on the performance of Strep A device. In this experiment, both conjugate pad and sample pad were pretreated with solutions containing different concentrations of Bis(2-(D-2-deoxyl-glucosaminyl)-PEG3-amide. Once the anti-Strep A-detector conjugate was sprayed on the pre-treated conjugate pad, different test devices were made by mixing different conjugate pads with different sample pads containing different amounts of Bis (2-(D-2-deoxyl-glucosaminyl)-PEG3-amide. These devices were tested with either a positive sample containing Strep A antigen or a sample containing mucin that would cause a false positive signal on the control devices without any Bis(2-(D-2-deoxyl-glucosaminyl)-PEG3-amide on either sample pad or conjugate pad.
Figure 9:
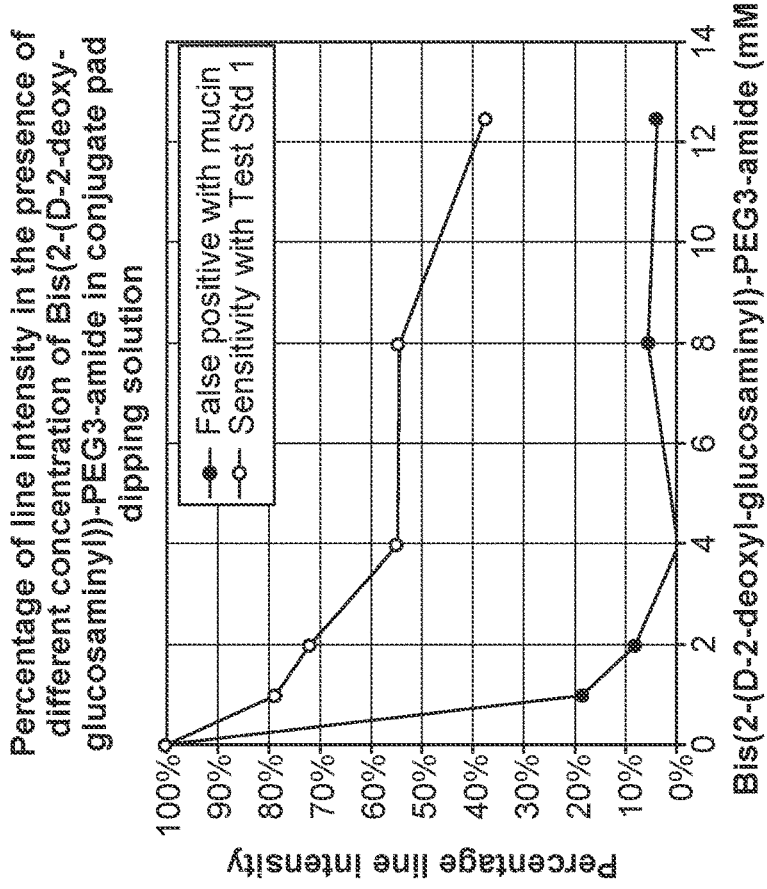
FIG. 9 shows the effect of adding different concentrations of Bis(2-(D-2-deoxy-glucosaminyl))-PEG3-amide to the conjugate pad dipping solution on the performance of a Strep A detection assay. The results in FIG. 8 indicate that high concentration of Bis(2-(D-2-deoxyl-glucosaminyl)-PEG3-amide in either sample pad dipping solution or conjugate pad dipping solution can effectively eliminate the false positive signal caused by mucin, but also inhibit the true signal. In this experiment, Bis(2-(D-2-deoxyl-glucosaminyl)-PEG3-amide at concentrations from zero to 12.5 mM was added to conjugate pad dipping solution. A positive sample containing Strep A antigen or a sample containing mucin that would cause a false positive was added to lateral flow devices made with conjugate pads treated with different concentrations of Bis(2-(D-2-deoxyl-glucosaminyl)-PEG3-amide. The results demonstrate that lower concentrations of the dimer can effectively eliminate mucin cross-reaction without much impact on the true sensitivity.
Figure 9:
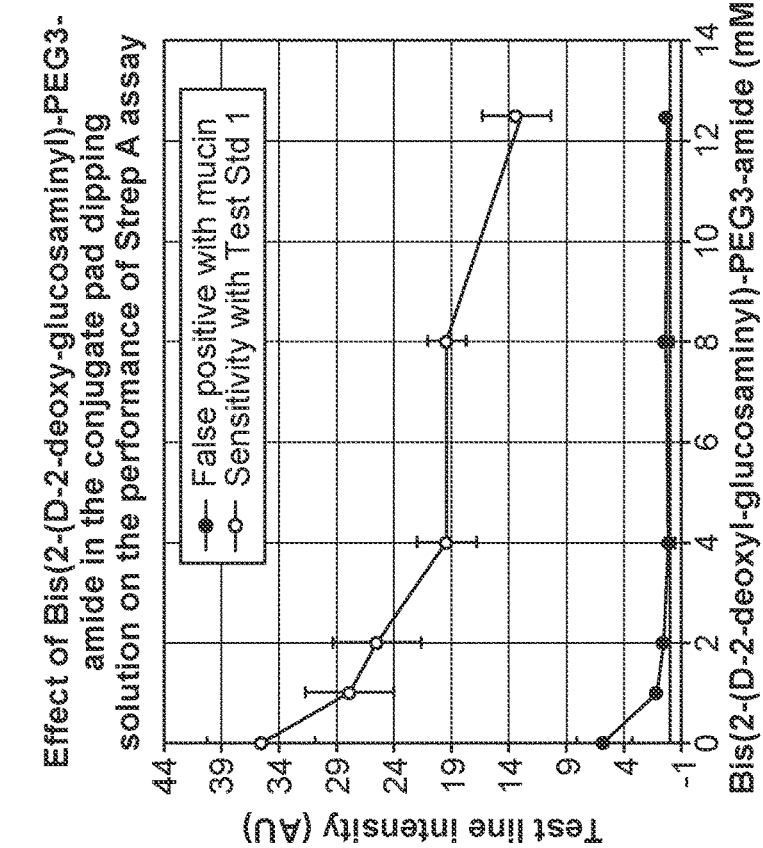

FIG. 8 shows the effect of adding Bis(2-(D-2-deoxyglucosaminyl)-PEG3-amide to the conjugate pad and sample pad dipping solution on the performance of Strep A device. These results demonstrate that the false positive signal is significantly reduced by adding the dimer to either the conjugate pad dipping solution and/or sample pad dipping solution. FIG. 9 demonstrates that lower concentrations of the Bis(2-(D-2-deoxy-glucosaminyl))-PEG3-amide dimer can effectively eliminate mucin cross-reaction without much impact on the true sensitivity when added to the conjugate pad dipping solution.

These results demonstrate that addition of 2-N-butanoyl-D-glucosamide, or Bis-(2-(D-2-deoxy-glucosaminyl))-PEG3-amide to an immunoassay for Strep A improves the specificity of the test for Group A *Streptococcus*, and unlike NAG, reduces the rate of false negatives. Thus, 2-N-butanoyl-D-glucosamide, or Bis-(2-(D-2-deoxy-glucosaminyl))-PEG3-amide can be used to effectively reduce false positives and false negatives in such tests. A skilled artisan will appreciate that the amount of antibody, 2-N-butanoyl-D-glucosamide or Bis-(2-(D-2-deoxy-glucosaminyl))-PEG3-amide, and sample can be adjusted for optimization of observing a positive signal from *S. pyogenes* while blocking false positives by 2-N-butanoyl-D-glucosamide, or Bis-(2-(D-2-deoxy-glucosaminyl))-PEG3-amide.

These results demonstrate that the compositions and devices disclosed here are useful in methods for detecting the presence of at least one Group A *Streptococcus* species in a biological sample.

Example 3: Inclusion of m-PEG4-Glucosamine, m-PEG6-Glucosamine, and m-PEG10-Glucosamine Reduces False Positive and False Negative Signals in Strep A Lateral Flow Immunoassay m-PEG4-glucosamine, m-PEG6-glucosamine, m-PEG10-glucosamine and m-PEG5000-glucosamine were tested for their ability to inhibit or block the binding of the anti-Strep A polyclonal antibodies in the Strep A immunoassay. Porcine mucin was dissolved in water and used as surrogate of human saliva sample. m-PEG4-glucosamine, m-PEG6-glucosamine, m-PEG10-glucosamine or m-PEG5000-glucosamine was added directly to the sample. Different concentrations of m-PEG4-glucosamine, m-PEG6-glucosamine, m-PEG10-glucosamine and m-PEG5000-glucosamine in an immunoassay were evaluated for inhibition of Strep A false positive signals.

Figure 10:
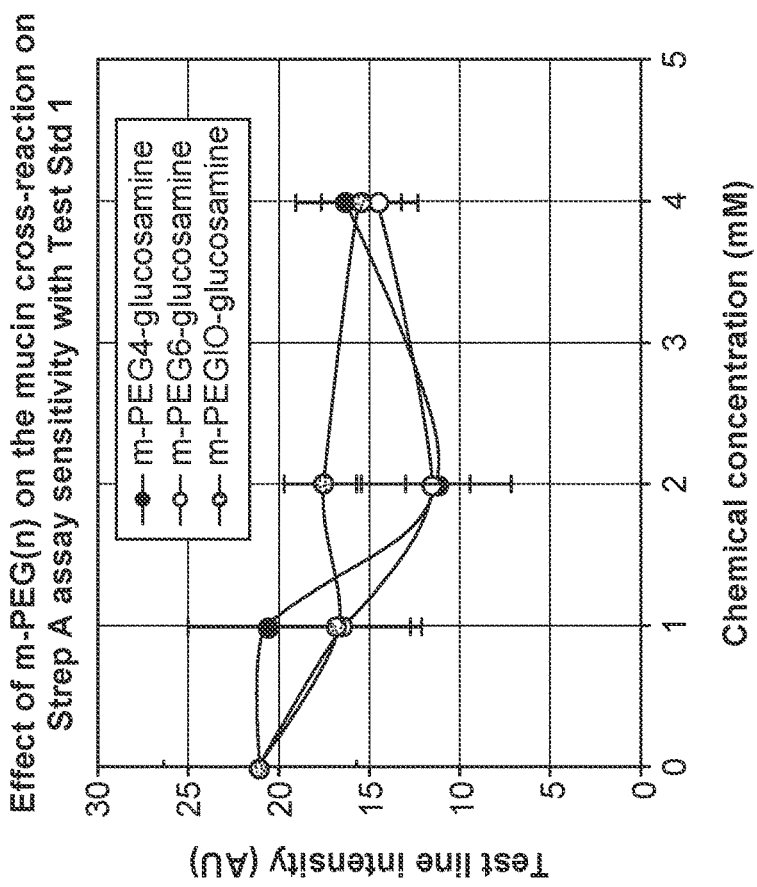
FIG. 10 shows the effect of m-PEGn(4, 6, 10)-glucosamine in the sample on the performance of Strep A assay. In this experiment, different concentration of m-PEGn(4,6, 10)-glucosamine were mixed with either a sample containing Strep A antigen or a mucin sample before they were added to the sample well of a lateral flow test device. The results show that these agents are effective in eliminating mucin cross-reaction without significant impact on the sensitivity of the Strep A assay.
Figure 10:
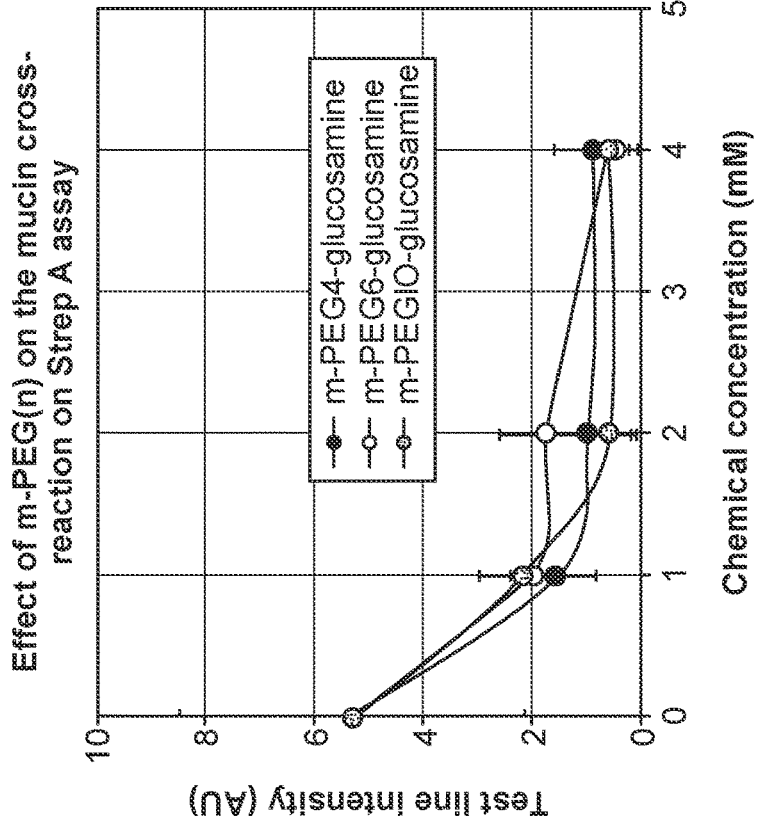
Figure 11:
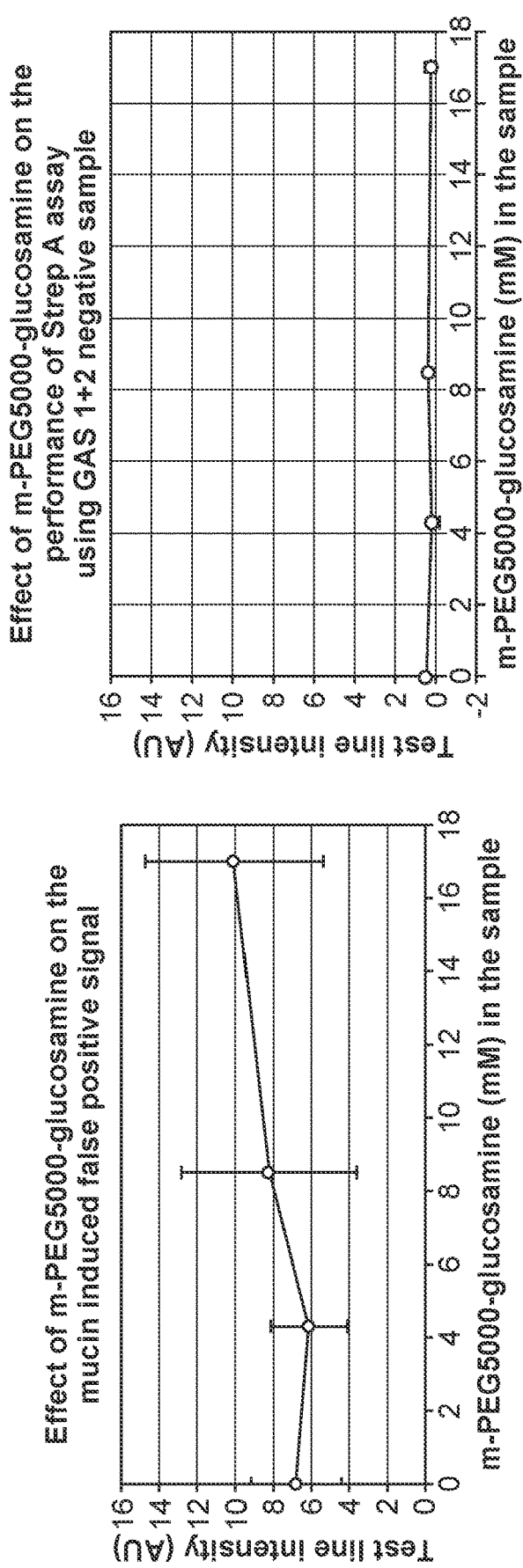
FIG. 11 shows the effect of m-PEG5000-glucosamine on the performance of a Strep A detection assay. The results demonstrate that m-PEG5000-glucosamine does not reduce the false positive signal caused by mucin, but instead increases the false positive signal in the presence of mucin. However, when mucin is not present, no false positive signal was observed when m-PEG5000-glucosamine was added to the extraction solution (GAS 1+2).

As shown in FIG. 10, different concentrations of m-PEGn (4,6,10)-glucosamine were mixed with either a sample containing Strep A antigen or a porcine mucin sample before they were added to the sample well of a lateral flow test device. The results indicate that m-PEG4-glucosamine, m-PEG6-glucosamine, and m-PEG10-glucosamine are effective in eliminating mucin cross-reaction without significant impact on the sensitivity of the Strep A assay. In contrast, m-PEG5000-glucosamine did not reduce the false positive signal caused by mucin, but instead increases the false positive signal in the presence of mucin. See FIG. 11. However, when mucin is not present, no any false positive signal was observed when added to the extraction solution (GAS 1+2).

These results demonstrate that addition of m-PEG4-glucosamine, m-PEG6-glucosamine, and m-PEG10-glucosamine to an immunoassay for Strep A improves the specificity of the test for Group A *Streptococcus*, and unlike NAG, reduces the rate of false negatives.

These results demonstrate that the compositions and devices disclosed here are useful in methods for detecting the presence of at least one Group A *Streptococcus* species in a biological sample.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

The terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. A method for detecting the presence of at least one Group A *Streptococcus* species in a biological sample comprising:
    (a) contacting the biological sample with a polyclonal antibody that specifically targets a Group A *streptococcus*-specific antigen and an amount of N-propionyl-D-glucosamine; or Bis-(2-(D-2-deoxy-glucosaminyl))-PEG3-amide; and
    (b) detecting binding of the polyclonal antibody to the Group A *streptococcus*-specific antigen, if present, in the sample;
    wherein detection of binding of the polyclonal antibody to the Group A *streptococcus*-specific antigen indicates the presence of at least one Group A *Streptococcus* species in the sample, and,
    wherein the amount of N-propionyl-D-glucosamine or Bis-(2-(D-2-deoxy-glucosaminyl))-PEG3-amide is an amount effective to reduce a false positive signal in the presence of mucin in the sample.

2. The method of claim 1, wherein the polyclonal antibody comprises a gold nanoparticle label, a chemiluminescent label, a radioactive label, a bioluminescent label, a fluorescent label, a chromogenic label, a spectroscopic label, a photochemical label, or an electrochemiluminescent label.

3. The method of claim 2, wherein the chemiluminescent label is selected from the group consisting of β-galactosidase, horseradish peroxidase (HRP), and alkaline phosphatase.

4. The method of claim 2, wherein the bioluminescent label is selected from the group consisting of aequorin, firefly luciferase, *Renilla* luciferase, red luciferase, luxAB, or nanoluciferase.

5. The method of claim 2, wherein the radioactive label is selected from the group consisting of $^{3}H$, $^{14}C$, $^{32}P$, $^{35}S$, $^{36}Cl$, $^{57}Co$, $^{131}I$ and $^{186}Re$.

6. The method of claim 1, wherein the biological sample is urine, saliva, sputum, mucous, a throat swab sample, whole blood, plasma, serum, amniotic fluid, semen, wound secretions, vaginal secretions, tears, or spinal fluid.

7. The method of claim 1, wherein binding of the polyclonal antibody to the Group A *streptococcus*-specific antigen is detected via enzyme-linked immunosorbent assay (ELISA) or Enzyme multiplied immunoassay technique (EMIT).

8. The method of claim 1, wherein the Group A *streptococcus*-specific antigen is selected from the group consisting of capsular polysaccharide (C-substance), cell wall peptidoglycan, lipoteichoic acid (LTA), M protein, fimbrial proteins, fibronectin-binding proteins, and cell-bound streptokinase.

9. The method of claim 1, wherein the biological sample is obtained from a subject suffering from or suspected of having a bacterial infection.

10. The method of claim 9, wherein the subject is human.

11. The method of claim 1, wherein the Group A *Streptococcus* species is *Streptococcus pyogenes* or *Streptococcus dysgalactiae*.

12. The method of claim 1, wherein contacting the biological sample with a polyclonal antibody that specifically targets a Group A *streptococcus*-specific antigen comprises applying the biological sample to a sample receiving zone of an immunoassay device comprising the sample receiving zone and a labeling zone, wherein the labeling zone comprises the antibody or antigen binding fragment that specifically targets a Group A *streptococcus*-specific antigen.

13. The method of claim 12, wherein the immunoassay device comprises a lateral flow device.

14. The method of claim 12, wherein the immunoassay device comprises N-propionyl-D-glucosamine, or Bis-(2-(D-2-deoxy-glucosaminyl))-PEG3-amide.

15. The method of claim 14, wherein the sample receiving zone comprises N-propionyl-D-glucosamine or Bis-(2-(D-2-deoxy-glucosaminyl))-PEG3-amide.

16. The method of claim 14, wherein the labeling zone comprises N-propionyl-D-glucosamine or Bis-(2-(D-2-deoxy-glucosaminyl))-PEG3-amide.

17. The method of claim 1, wherein contacting the biological sample with an effective amount of N-propionyl-D-glucosamine or Bis-(2-(D-2-deoxy-glucosaminyl))-PEG3-amide comprises adding an effective amount of N-propionyl-D-glucosamine or Bis-(2-(D-2-deoxy-glucosaminyl))-PEG3-amide directly to the biological sample.

18. The method of claim 17, wherein adding an effective amount of N-propionyl-D-glucosamine or Bis-(2-(D-2-deoxy-glucosaminyl))-PEG3-amide directly to the biological sample comprises adding N-propionyl-D-glucosamine or Bis-(2-(D-2-deoxy-glucosaminyl))-PEG3-amide to an extraction reagent and combining the biological sample with said extraction reagent.

19. The method of claim 1, wherein the biological sample comprises epithelial cells originating from the tongue, cheek or teeth.

20. The method of claim 1, wherein the addition of N-propionyl-D-glucosamine or Bis-(2-(D-2-deoxy-glucosaminyl))-PEG3-amide reduces false positive results.

21. The method of claim 1, wherein the addition of N-propionyl-D-glucosamine or Bis-(2-(D-2-deoxy-glucosaminyl))-PEG3-amide does not increase false negative results.

22. A method for detecting the presence of *Streptococcus pyogenes* in a biological sample comprising:

(a) applying a throat swab sample or saliva sample to a sample receiving zone of a lateral flow immunoassay device comprising the sample receiving zone and a labeling zone, wherein the labeling zone comprises a polyclonal antibody that specifically targets a Group A *streptococcus* capsular polysaccharide (C-substance), wherein the antibody or antigen binding fragment comprises a gold nanoparticle label, and wherein the sample receiving zone or labeling zone comprises an amount of N-propionyl-D-glucosamine; and (b) detecting binding of the antibody or the antigen binding fragment to the Group A *streptococcus* capsular polysaccharide (C-substance), if present, in the sample;

wherein detection of binding of the polyclonal antibody indicates the presence of *Streptococcus pyogenes* in the sample, and wherein the amount of N-propionyl-D-glucosamine is an amount effective to reduce a false positive signal in the presence of mucin in the sample.

* * * * *